(12) United States Patent
Grosman et al.

(10) Patent No.: US 11,641,814 B2
(45) Date of Patent: May 9, 2023

(54) MAINTAINING POPULATIONS OF NATURAL ENEMIES ON PLANTS

(71) Applicant: BioBee Sde Eliyahu Ltd., Emek Hamaayanot (IL)

(72) Inventors: Amir Grosman, Emek Hamaayanot (IL); Shimon Steinberg, Emek Hamaayanot (IL); Michael Salinger Bubnov, Emek Hamaayanot (IL); Amit Sade, Emek Hamaayanot (IL); Yariv Dan, Emek Hamaayanot (IL); Efrat Gilboa, Emek Hamaayanot (IL)

(73) Assignee: BIO-BEE SDE ELIYAHU LTD, Sde Eliyahu (IL)

( * ) Notice: Subject to any disclaimer, the term of this patent is extended or adjusted under 35 U.S.C. 154(b) by 60 days.

(21) Appl. No.: 17/001,976

(22) Filed: Aug. 25, 2020

(65) Prior Publication Data

US 2020/0383279 A1 Dec. 10, 2020

Related U.S. Application Data

(63) Continuation-in-part of application No. PCT/IL2019/050215, filed on Feb. 26, 2019.
(Continued)

(51) Int. Cl.
*A01G 13/10* (2006.01)
*A01G 9/12* (2006.01)
(Continued)

(52) U.S. Cl.
CPC .......... *A01G 13/105* (2013.01); *A01G 9/128* (2013.01); *A01K 67/033* (2013.01); *A01M 99/00* (2013.01)

(58) Field of Classification Search
CPC ..... A01G 13/105; A01G 9/128; A01M 99/00; A01K 67/033
See application file for complete search history.

(56) References Cited

U.S. PATENT DOCUMENTS

| 8,733,283 | B2 * | 5/2014 | Fidgett ........... A01N 63/16 119/6.5 |
| 9,781,937 | B2 * | 10/2017 | Bolckmans ....... A01N 63/16 |
| 2005/0178337 | A1 * | 8/2005 | Wright .......... A01K 67/033 119/6.5 |

FOREIGN PATENT DOCUMENTS

| EP | 3053439 A1 * | 8/2016 | ........ A01K 67/033 |
| EP | 3053439 | 1/2018 | |

(Continued)

OTHER PUBLICATIONS

Adar et al., "Pollen on-twine for food provisioning and oviposition of predatory mites in protected crops", Feb. 20, 2014, vol. 59, Issue 3, pp. 307-317, Springer-Verlag.
(Continued)

*Primary Examiner* — Monica L Perry
*Assistant Examiner* — Aaron M Rodziwicz
(74) *Attorney, Agent, or Firm* — Pearl Cohen Zedek Latzer Baratz LLP

(57) ABSTRACT

Methods and platforms are provided for maintaining a population of natural enemies on plants, prior and/or parallel to an occurrence of respective prey pests, by associating with the plants platform(s) comprising mechanical support(s) with attached feeding elements for the natural enemies. The platform may be configured to keep the
(Continued)

feeding elements close to but not on the plants, protecting them and enhancing the distribution efficiency and life time, while maintaining good availability of the feeding elements to the natural enemies. Various features may enhance supporting the natural enemies' population prior and/or parallel to the occurrence of the pest prey such as olfactory and/or visual cues to the feeding elements as well as sheltering elements such as artificial domatia on the surface of the mechanical support—to enhance biological pest control. Moreover, methods for preparing decapsulated *Artemia* cysts as feed for predatory arthropods are provided.

13 Claims, 25 Drawing Sheets

Related U.S. Application Data

(60) Provisional application No. 62/661,105, filed on Apr. 23, 2018, provisional application No. 62/634,944, filed on Feb. 26, 2018.

(51) Int. Cl.
*A01K 67/033* (2006.01)
*A01M 99/00* (2006.01)

(56) References Cited

FOREIGN PATENT DOCUMENTS

| ES | 2392973 A1 * | 12/2012 | ........... A01G 13/105 |
|----|----|----|----|
| GB | 2393890 A * | 4/2004 | ........... A01K 67/033 |
| KR | 100597613 | 6/2006 | |
| KR | 100597613 B1 * | 7/2006 | |
| KR | 100720977 B1 * | 5/2007 | |
| KR | 100732601 B1 * | 6/2007 | |

OTHER PUBLICATIONS

Bruggeman et al., "Improvements in the decapsulation technique of Artemia cysts", The Brine Shrimp Artemia, Universa Press. Wetteren, Belgium, Dec. 31, 1980, vol. 3, pp. 261-269.
De Clercq et al., "Notritional value of bringe shrimp cysts as a factitious food for Orius Laevigatus (Heteroptera; Anthocoridae)", Aug. 2005, vol. 15, No. 4, pp. 467-479, Biocontrol Selene and Technology, Taylor & Francis.
Nguyen et al., "Artificial and factitious foods support the development and reproduction of the predatory mite Amblyseius swirskii", 2014, Exp Appl Acarol, vol. 62, pp. 181-194.
Vandekerkhove et al., "Artemia cysts as an alternative food for the predatory bug Macrolophus pygmaeus", 2008, J. Appl. Entomol, pp. 1-10.
Vangansbeke et al., "Performance of the predatory mite Amblydromalus limonicus on factitious foods", BioControl 2014, vol. 59, No. 1, pp. 67-77.
Janssen et al., "Time scales of associating food and odor by predator communities in the field", Behavioral Ecology 2014, vol. 25, No. 5, pp. 1123-1130.
Messelink et al., "Approaches to conserving natural enemy populations in greenhouse crops: current methods and future prospects", BioControl, May 8, 2014, vol. 59, pp. 377-393.
Simpson et al., "Attract and reward: combining chemical ecology and habitat manipulation to enhance biological control in field crops", Jan. 25, 2011, Journal of Applied ecology, vol. 48, Issue 3.
Coutteau et al., "Manual on the Production and Use of Live Food for Aquaculture", FAO fisheries technical paper, Rome, Dec. 31, 1996, 361.
Castane et al., "The brine shrimp Artemia sp. As alternative prey fot rearing the predatory bug Macrolophus caliginosus", Biological Control 38, Apr. 26, 2006, pp. 405-412.
International Search Report for PCT application No. PCT/IL2019/050215, dated Jun. 20, 2019.
Lavens, P.; Sorgeloos, P. (1996). Manual on the production and use of live food for aquaculture. FAO Fisheries. Technical Paper 361, Rome.

* cited by examiner

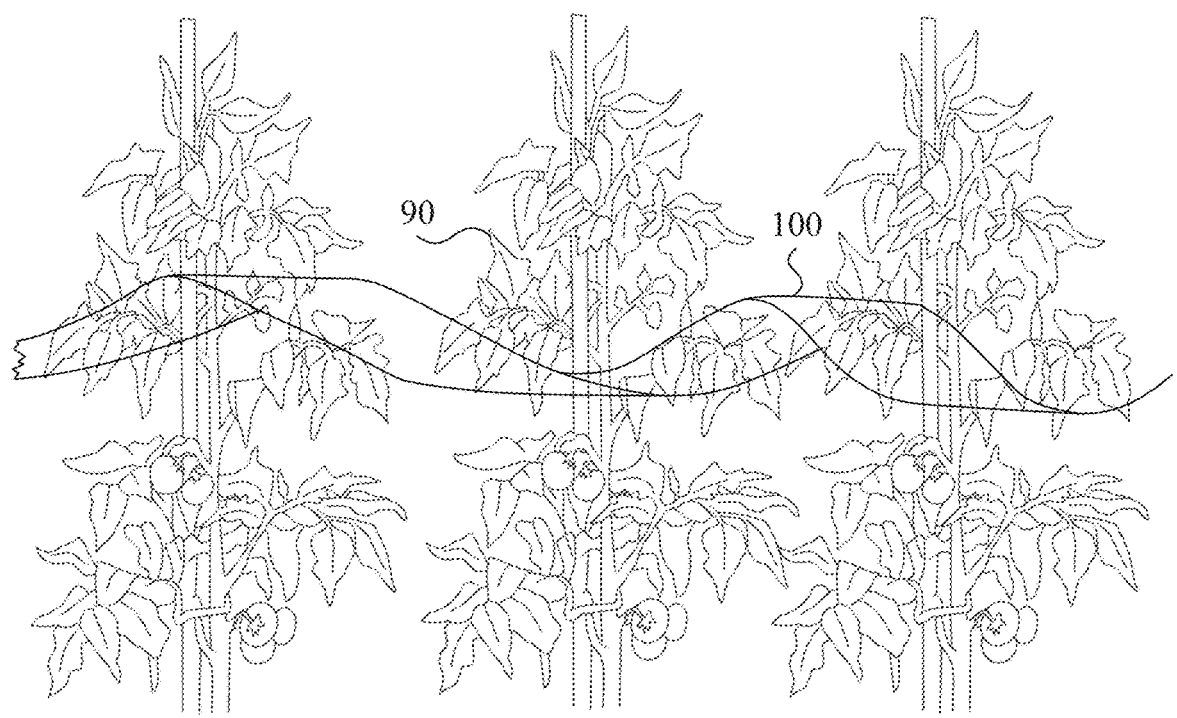
Figure 1B
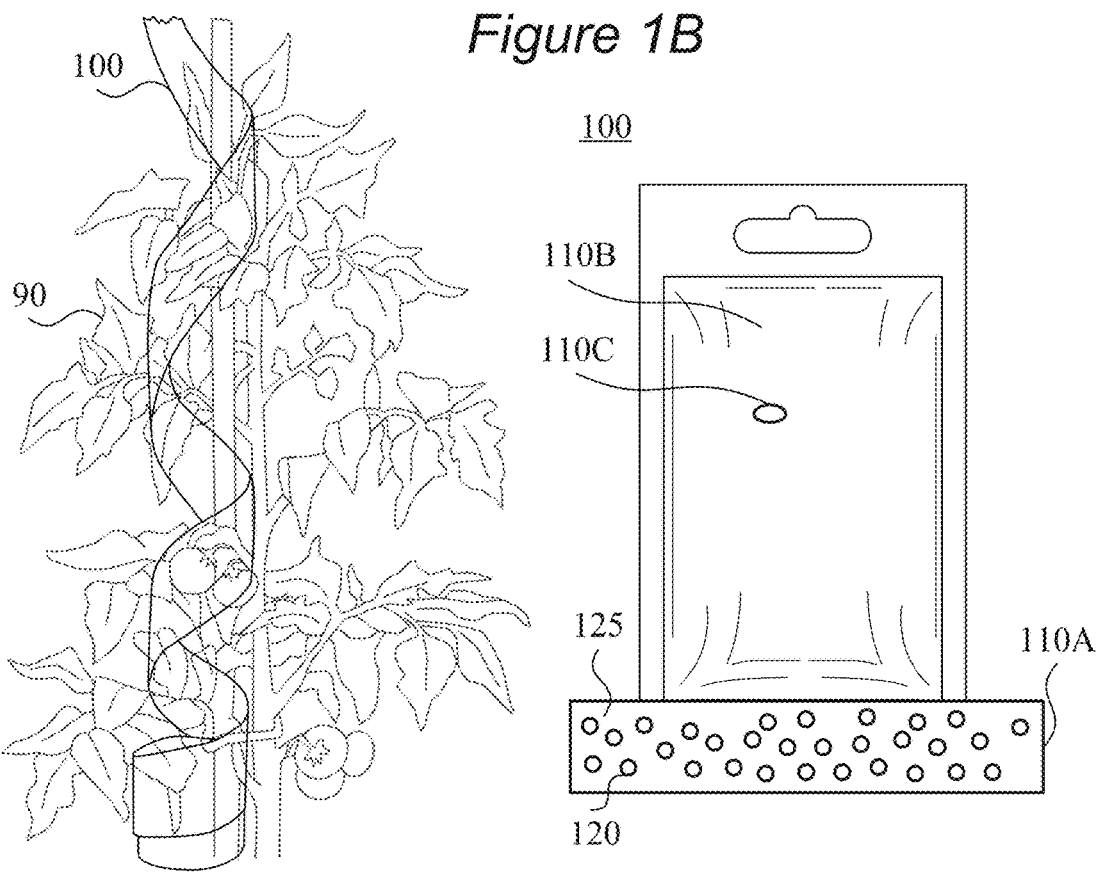
Figure 1C
Figure 1D

MAINTAINING POPULATIONS OF NATURAL ENEMIES ON PLANTS

RELATED APPLICATIONS

This application is a continuation-in-part of PCT/IL2019/050215, filed Feb. 26, 2019, which claims the benefit of U.S. Provisional Application Nos. 62/634,944, filed Feb. 26, 2018 and 62/661,105, filed Apr. 23, 2018.

BACKGROUND OF THE INVENTION

1. Technical Field

The present invention relates to the field of biological control, and more particularly, to means and methods to support early establishment of natural enemies on crops

2. Discussion of Related Art

Growers that apply biological control normally have to wait until pests appear on their crop, before they can successfully introduce predators to control the pests. For this reason, pests normally have a head start—they can start developing and reproducing in an enemy-free crop. The success of biological pest control therefore depends on intensive scouting and release of high numbers of predators once pests have been detected and at least partly established.

SUMMARY OF THE INVENTION

The following is a simplified summary providing an initial understanding of the invention. The summary does not necessarily identify key elements nor limits the scope of the invention, but merely serves as an introduction to the following description.

One aspect of the present invention provides a method of maintaining a population of natural enemies on plants, prior and/or parallel to an occurrence of respective prey pests, the method comprises associating with the plants a platform comprising at least mechanical support with attached feeding elements for the natural enemies.

One aspect of the present invention provides a method comprising preparing decapsulated *Artemia* cysts as feed for predatory arthropods which is effective as feed for at least three weeks post application (possibly depending on relative humidity), by: hydrating the *Artemia* cysts, decapsulating the hydrated *Artemia* cysts using cooled chemicals, followed by separation and neutralization of the decapsulated cysts, drying the decapsulated cysts mildly, maintaining their quality as feed according to specified criteria, and preparing the dried decapsulated cysts as the feeding elements.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 1A-1I are high-level schematic illustrations of a platform for maintaining a population of natural enemies on plants, prior and/or parallel to an occurrence of respective prey pests, according to some embodiments of the invention.

DETAILED DESCRIPTION OF THE INVENTION

Figure 1A:
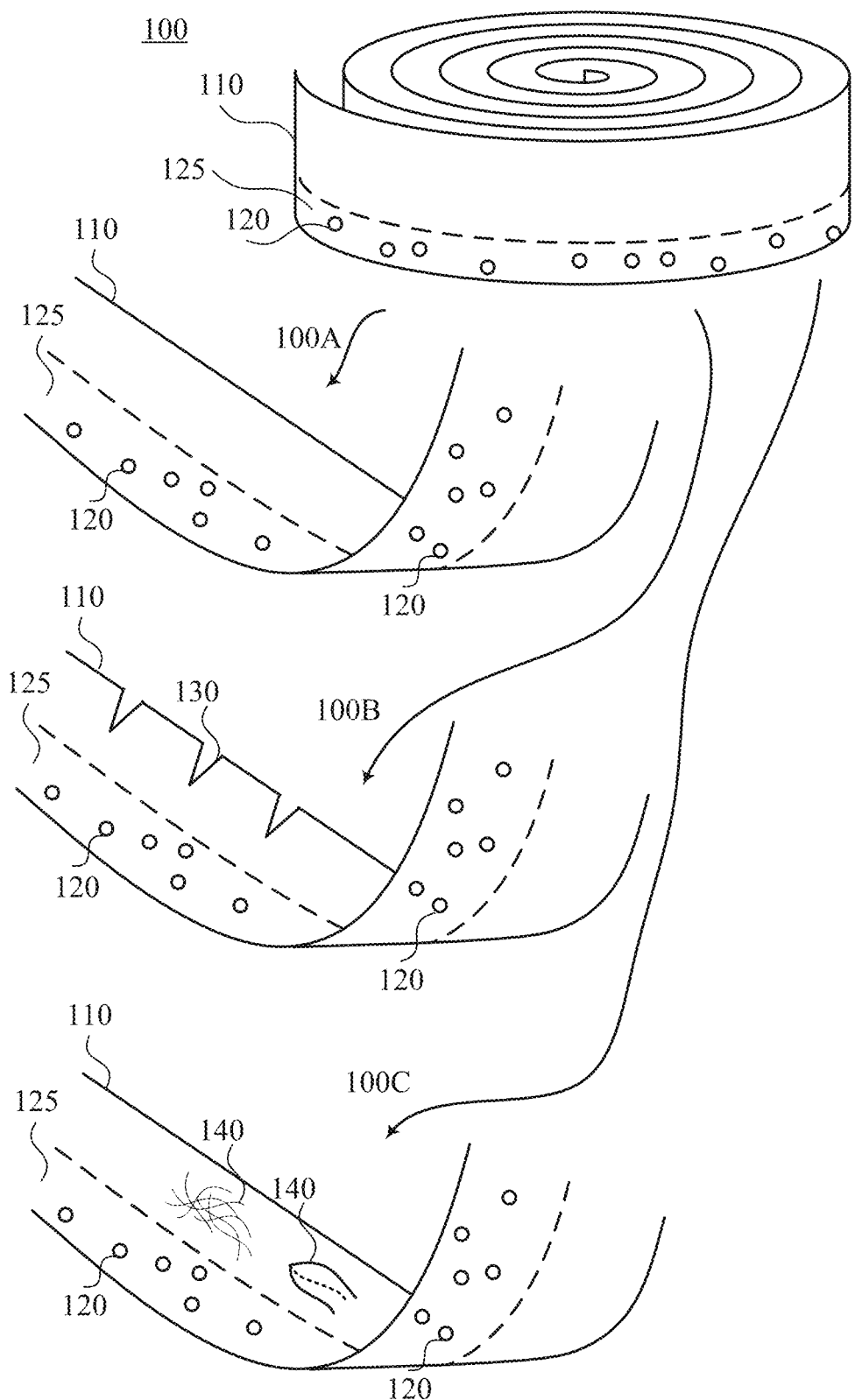
Figure 1A:
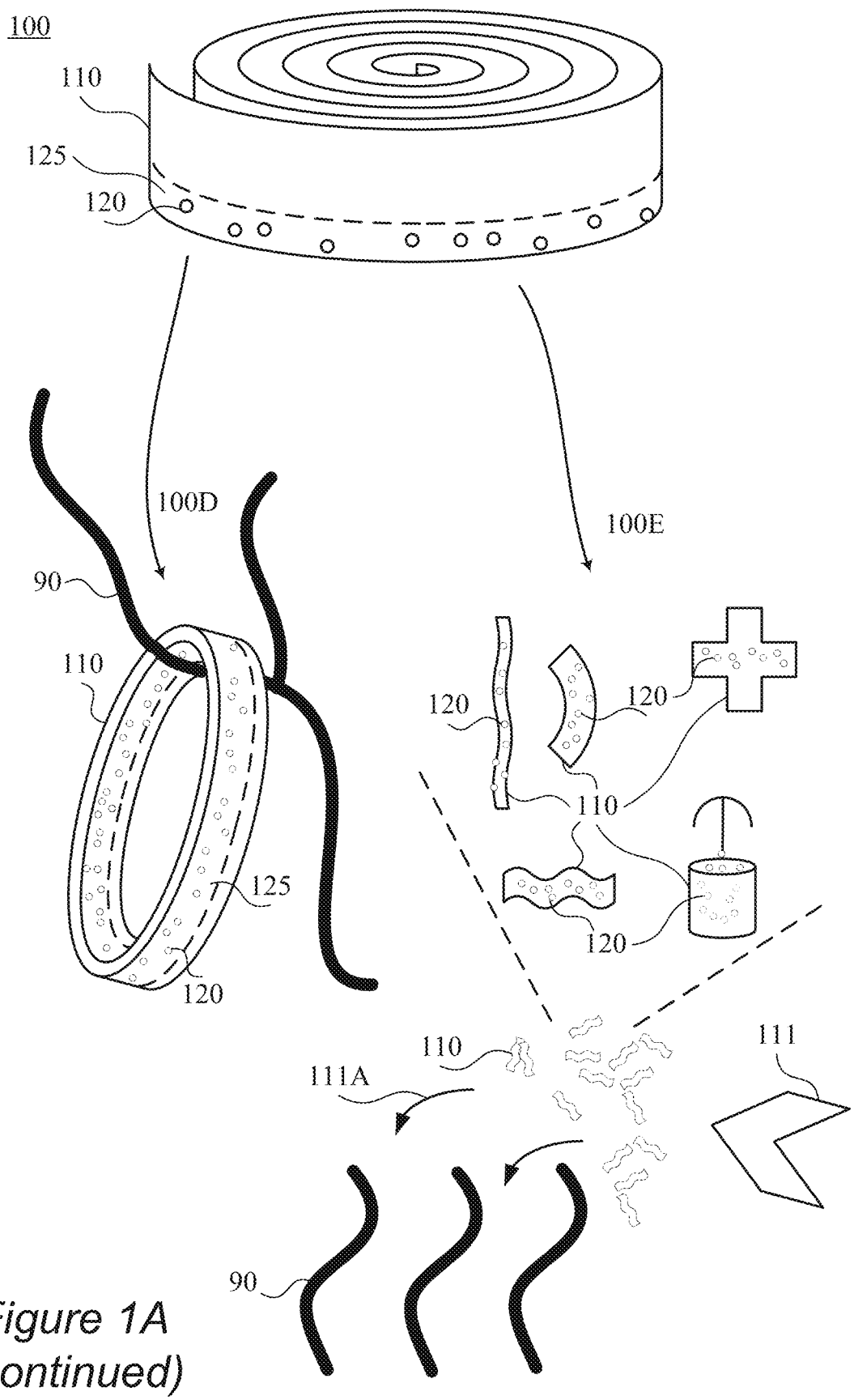

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Embodiments of the present invention provide efficient and economical methods and mechanism for supporting early establishment of natural enemies on crops and thereby provide improvements to the technological field of biological pest control. Methods and platforms are provided for maintaining a population of natural enemies on plants, prior and/or parallel to an occurrence of respective prey pests or hosts, by associating with the plants platform(s) comprising mechanical support(s) with attached feeding elements for the natural enemies. The platform may be configured to keep the feeding elements close to but not on the plants, protecting them and enhancing the distribution efficiency and life time, while maintaining good availability of the feeding elements to the natural enemies. Various features may enhance supporting the natural enemies' population prior to the occurrence of the pest prey such as olfactory and/or visual cues to the feeding elements as well as sheltering elements such as artificial domatia on the surface of the mechanical support. Moreover, methods for preparing decapsulated *Artemia* cysts as feed for predatory arthropods are provided. Disclosed platforms are generic, easy to apply to the plants, distribute the natural enemies' food efficiently and for a long duration to enhance the "standing army" approach of biological pest control.

FIGS. 1A-1I are high-level schematic illustrations of a platform 100 for maintaining a population of natural enemies on plants, prior and/or parallel to an occurrence of respective prey pests, according to some embodiments of the invention. As illustrated e.g., in FIG. 1A, Platform 100 comprises one or more mechanical supports 110 with attached feeding elements 120 for the natural enemies. Feeding elements 120 comprise alternative food sources, on the crops, which enable early establishment and maintenance of natural enemies (such as predatory mites or predatory bugs) on the plants, or near the plants, before their prey pests, typically pest insects and mites, arrive to the plants. Once the pests arrive, they may be immediately attacked by their natural enemies—preventing an initial proliferation stage of the pest prey which may occur when natural enemies are applied curatively to infestation. Disclosed platforms 100 may be applied to a wide range of plants, principally crop plants, such as annuals (e.g., vegetables) as well as possibly flowers—grown in greenhouses, net houses or possibly in the open field.

Platforms 100 are generally used for supporting generalist predators, which can be sustained on feeding elements 120 other than their natural prey pest, at least for some time, such as predacious and/or omnivorous natural enemies, e.g., phytoseiid predatory mites, mirid predatory bugs and/or antochorid predatory bugs (minute pirate bugs), lacewings (Neuroptera, e.g, *Chrysoperla*), syrphid flies (Syrphidae, Diptera), etc. Examples for feeding elements 120 which may be provided as food for such generalist natural enemies (illustrated e.g., in FIGS. 4A, 4C, 4E, 9C and 9D) comprise e.g., any of live or inactivated eggs of insects (e.g., *Ephestia kueheniella* eggs) or mites, live prey-like astigmatid mites and/or their respective diets, alternative prey species such as astigmatid mites, pollen (e.g., *Typha* pollen), decapsulated shrimp cysts (e.g., brine shrimp *Artemia* sp.), nutrients (e.g., carbohydrates such as sugars, honey) and/or artificially composed diets designed to feed natural enemies, as well as alternative foods described in Nguyen et al. 2014 (Artificial and factitious foods support the development and reproduction of the predatory mite *Amblyseius swirskii*, Experimental Applied Acarology 62:181-194) and Messelink et al. 2014 (Approaches to conserving natural enemy populations in greenhouse crops: current methods and future prospects, BioControl 59(4): 377-393) incorporated herein by reference in its entirety. It is noted that processed *Artemia* cysts have a long shelf life (e.g., a year, three years, or more), which may simplify the storing and using of platforms 100. Combinations of the food sources provided above are likewise part of the present disclosure, and may be adjusted according to the diet requirements of the used natural enemies. Platforms 100 may be used to introduce predators before their respective prey is detected on the plants and/or to boost predator populations once prey is detected on the plants, to enhance pest control.

In certain embodiments, platforms 100 may comprise mechanical support 110 configured as a strap or a tape with region(s) 125 in which feeding elements 120 are attached, such as narrow adhesive edge(s) to which feeding elements 120 are attached, on one or both sides of the tape, as illustrated in FIG. 1A and showed in examples in FIGS. 3A-3E. Accordingly, platforms 100 may comprise tape 110 with alternative food 120 for specified natural enemies glued to one or both of its sides. In various embodiments, attaching feeding elements 120 to mechanical support 110 may comprise securing feeding elements 120 to mechanical support 110 using static electricity alone or by wetting mechanical support 110, to avoid use of glue. In certain embodiments, platforms 100 may be configured to be bio-degradable, e.g., by using bio-degradable materials for mechanical support 110 and attaching feeding elements 120 to mechanical support 110 in a way that maintain biodegradability, e.g., using a biodegradable glue or avoiding use of glue with electrostatic or wetting-based attachment.

Platforms 100 may be applied on the crop by securing it on one or more plants in a plant row and deploying it along the row, so that it forms a continuous food strip touching all, most or some plants in the row. Platforms 100 may be applied in a way that enables easy movement of the predators between platform 100 and the crop plants (e.g., platform 100 may be in contact with each plant or with most of the plants). As the food (feeding elements 120) is glued to the tape, there is no wastage of food falling on the soil. Moreover, platforms 100 which are symmetrical in that the food is glued on both sides of the tape may simplify their application by leaving no room for mistake between upper or lower sides and by applying half of the food on a side of the tape which does not absorb UV (ultraviolet) radiation and is therefore effective as feed longer than exposed feed. Furthermore, as in disclosed application method, most food does not contact the leaf surface, it is exposed to relatively lower humidity, and is therefore more durable than food spread directly on the leaves. In certain embodiments, feeding elements 120 may be pre-treated with insect-safe preservatives, to further enhance their durability as effective feed on mechanical support 110 for the natural enemies. In certain embodiments, carriers such as sawdust and/or sand (see, e.g., FIGS. 4D, 5A, 5B) may be attached to mechanical support 110 alongside feeding elements 120, and the carriers may be pre-treated with insect-safe preservatives (avoiding direct treatment of feeding elements 120 themselves), to further enhance their durability as effective feed on mechanical support 110 for the natural enemies. Examples for insect-safe food preservatives comprise, e.g., methylparaben and potassium sorbate (found by the inventors to be safe for the predatory mite *Amblyseius swirskii* and for the predatory bugs *Macrolophus pygmeus* and *Orius laevigatus*, see, e.g., FIGS. 10B, 10C and 10D). The inventors estimate that in some embodiments, the enhanced food durability may result in an application frequency of once every four, eight and/or ten weeks, or possibly even longer (see, e.g., FIGS. 3B and 3D). The application of platform 100 to the plants may be carried out after planting and/or once the foliage is developed adequately to have sufficient contact with mechanical support 110.

In certain embodiments, platform 100 may be configured to provide at least one of the feeding elements, oviposition substrate and/or shelters for the natural enemies, at least during part of the use period of platform 100. In certain embodiments, some of platforms 100 may be configured to provide one or more of the feeding elements, ovipositioning substrate and/or shelters for the natural enemies, while some other of platforms 100 may be configured to provide different resources (e.g., some platforms may provide feeding elements while other platforms may provide shelters and/or ovipositioning substrate, and still other platforms may provide both).

FIG. 1A illustrates non-limiting schematic examples for configurations of platform 100 such as double-sided mechanical support 110 of platform 100A configured as a strap with feeding elements 120 on regions 125 (e.g., adhesive regions, or regions with attached adhesive tape) on both sides thereof (e.g., strap mechanical support 110 may comprise two adhesive strips along the strap, one on each side of the strap).

Non-limiting schematic examples for platform configurations comprise notched mechanical support 110 of platform 100B configured to have attachment elements 130 such as notches or cuts configured to enhance the application and clinging of platform 100 to the plants. Attachment elements 130 may be configured, e.g., shaped, according to plant structural characteristics (e.g., stem width, leaf size, typical stem-leaf angles, stem flexibility etc.) to optimize the stability of association between mechanical support 110 and the plants, and possibly to support placing mechanical support 110 at specified height or plant location to maximize its efficiency (e.g., with respect to typical pest infestation location, with respect to the sprinkling system, etc.).

Non-limiting schematic examples for platform configurations comprise mechanical support 110 of platform 100C configured to have surface and/or volume features 140 such as filamentous protrusions (e.g., fibers, hairs or threads) and/or artificial domatia (structured protrusions, notches, cavities, indentations, crevices, corrugations, internal volume etc.) for the natural enemies to take shelter or breed in, e.g., simulating natural shelters or domatia for the used natural enemies. In addition to its application for effectively providing alternative food for generalist predators, platform 100 may be further configured to improve predator establishment on crops by providing surface features 140 as shelters (domatia) configured to function as hairs or cavities between the leaf tissue and veins. Adding such shelters to platform 100 may increase the tendency of predators to stay on it and find the food even more easily. It may also help predators establish on crops which lack natural domatia. For example, predatory mites often prefer to lay their eggs on leaf hairs. Adding fibers (as surface features 140) to platform 100 may provide predatory mites with a suitable egg laying substrate, and improve their establishment on some crops. In certain embodiments, platform 100 may comprise surface features 140 that comprise egg-laying (oviposition) substrate for predators that typically lay their eggs inside the plant tissue, such as predatory bugs. Such surface features 140 may be configured to provide sufficient volume and appropriate surface and material characteristics that correspond to the ovipositioning preferences of the respective predator arthropods.

In certain embodiments, illustrated schematically in platform embodiments 100D, platform 100 may comprise multiple mechanical supports 110 with attached feeding elements 120 having form(s) configured to be easily applicable and affixable to certain plants 90 mechanical features, such as rings, hooked structures, meshes etc. The shape and/or flexibility of mechanical supports 110 may be configured with respect to optimized application location on or near the plant, and with respect to parameters such as plant characteristics, irrigation characteristics etc.

In certain embodiments, illustrated schematically in platform embodiments 100E, platform 100 may comprise multiple small mechanical supports 110 (e.g., having a size scale of a few centimeters, e.g., under 10 cm, possible under 30 cm, possibly thin and long threads or narrow straps which may extend in length beyond 30 cm and have widths of a few cm or less) with attached feeding elements 120, and having form(s) optionally configured to be easily attachable to plants 90 when applied 111A by a distributing means 111 such as an air blower(s) and/or drone(s) 111, configured to distribute a large number of small mechanical supports 110, e.g., over the plants and/or crops. Small mechanical supports 110 may be two- and/or three-dimensional, as illustrated schematically in FIG. 1A, and may comprise flat, corrugated or enclosing elements, including capsules, granules and/or particles configured to be distributed aerially and be attached to the plants upon contact. It is noted that aerially distributed small mechanical supports 110 may be configured to be attachable to the plants, or be configured to drop around the plants (e.g., as capsules) in or on which natural enemies may feed and/or from which natural enemies may hatch. In certain embodiments, multiple small-scale mechanical supports 110 may be associated with the plants or distributed around the plants by blowing them over the crop and allowing them to passively descend on the crop and get associated therewith, e.g., by getting entangled in plant parts or being distributed in the vicinity of the plants.

While possibly leading to more waste due to supports 110 which do not cling to plants 90, platforms 100E may be efficient in covering larger crops and/or reaching areas of the crop which are not easily reached by manual, one-by-one application of supports 110. Small mechanical supports 110 may have one or more shapes, as illustrated schematically in FIG. 1A, possibly having attachment means such as spikes, arrowheads, twisted or curved shapes, filaments, rings, hooked structures, meshes etc., possibly adapted to plant morphology and distribution method, which facilitate attachment of small mechanical supports 110 to plants 90 upon their distribution thereupon. In certain embodiments, strap or sheet-like support 110 may be cut into small pieces to provide small mechanical supports 110, with feeding elements 120 attached to support 110 before, during or after preparing small mechanical supports 110. The shape and/or flexibility of mechanical supports 110 may be configured with respect to optimized application location on or near the plant, and with respect to parameters such as plant characteristics, irrigation characteristics, distribution means characteristics, etc.

In certain embodiments, platform 100 may comprise multiple natural enemies' feeding stations configured as multiple mechanical supports 110 with attached feeding elements 120 which may be in the crop environment, but not necessarily in contact with the crop plants. Feeding station platforms 100 may be applied in combination with plant-contacting platforms 100 and/or platforms 100 in the close vicinity of the crop plants. Feeding station platforms 100 may be configured to create a patchy distribution of food within the crop environment, possibly associated with corresponding visual and/or olfactory cues.

FIGS. 1B-1I are high-level schematic illustrations of platform 100 for maintaining a population of natural enemies on plants 90, prior and/or parallel to an occurrence of respective prey pests, according to some embodiments of the invention.

FIG. 1B illustrates schematically the application of one or more tape-shaped mechanical supports 110 across multiple plants, possibly attached to one or more plants 90 and in close association with other plants 90. Tape-shaped mechanical supports 110 may be attached to plants 90 manually, possibly assisted by attachment elements 130 and/or by combination of the mechanical properties of mechanical supports 110 and of respective plants 90. Tape-shaped mechanical supports 110 may be associated with plants 90 at different heights, possibly sequentially during the growth of plants 90. The illustrated non-limiting application is mainly horizontal.

FIG. 1C illustrates schematically the application of one or more tape-shaped mechanical supports 110 on one or more plants 90 in vertical manner, as a non-limiting illustration. Vertical application of tape-shaped mechanical supports 110 may be carried out on one or more plants per mechanical support 110. Mechanical supports 110 may be flexibly associated with plant(s) 90 and provide feeding elements 120 along plant(s) 90.

FIG. 1D illustrates schematically the application of one or more sachet-shaped mechanical supports 110, as a non-limiting illustration. Mechanical support 110 may comprise a supporting part 110A supporting exposed feeding elements 120 and a sachet part 110B configured to release the natural enemies (predators) gradually. Sachet part 110B may comprise early developmental stages of the predators, possibly even eggs of natural enemies, and possibly supporting feeding elements 120 or other feeding elements. Sachet part 110B may have a small opening 110C configured to allow gradual release (possibly gradual hatching) of the predators therefrom. Providing feeding elements 120 externally in proximity to sachet part 110B may support and enhance the continuous release of the predators and support the growing population. In certain embodiments, internal feeding elements 120 in sachet 110B may be configured to support a breeding colony of predators within the sachets.

It is noted that while sachets with predatory mites are known, disclosed configurations of sachets with *Artemia* cysts, and/or possibly other or additional types of feeding elements—as internal and/or external feeding elements 120 are not taught by the prior art and provide a much more effective and sustainable way to support the population of predatory natural enemies on the crops.

Prior art methods to apply predatory mites, which play a key role in biological control, on crops—are applying the mites directly on the leaves (foliar application) or applying the mites using a slow release system such as a rearing sachet with a colony of predatory mites which reproduce and leave the sachet gradually through a small exit hole. Prior art sachets which support reproduction of the predatory mites include an active population of astigmatid mites (one or two species) as food for the predatory mites, and additional food for the (prey) astigmatid mites themselves, normally bran and yeast-based diets. Thus, conventional rearing sachets contain three trophic levels—predators, prey and prey-diets. When the asitgmatid mite population is depleted, there is no more food for the predators and their colony collapses. Typical prior art sachets produce predatory mites for a period of 4-8 weeks and differ from each other by the species of astigmatid mite used, type of sachet and sachet material, and other factors. A major challenge in the field concerns the production of sachets that are effective for longer periods and/or release larger numbers of predators at a given period of time.

Advantageously, disclosed platforms 100 in sachet configuration utilize decapsulated cysts of the brine shrimp *Artemia* spp. as feeding elements 120 for predatory mites for the first time. High quality *Artemia* cysts were shown by the inventors to provide adequate food for predatory mites (see e.g., FIG. 6A below), enabling to sustain populations of predatory mites for multiple generations. It is noted that in prior art such as Nguyen et al. 2014, has poor durability post-application, due to an inadequate drying method which causes mechanical damage to the cysts, and because preservatives were not applied. Prepared using the disclosed production method, the inventors were able to reach *Artemia* cysts which have a long shelf life, remaining in good condition for at least three years when refrigerated and durable for ca. four weeks when exposed, e.g., upon foliar application, to sun-light and relatively high humidity and durable for ca. eight weeks when prepared with food preservatives which decrease the development of mold on the cysts while being safe for the predatory mites. Disclosed application of the *Artemia* cysts as internal feeding elements 120 in the sachets (protected from sun-light and kept in relatively dry conditions) may reach viability periods of three to six months—extending prior art sachet population viability threefold or more. Using the *Artemia* cysts may also be simpler and more effective than prior art maintaining of the additional astigmatid mites' population in prior art sachets.

Additional advantages of *Artemia*-based sachets as platforms 100 include the higher density of predators per sachet (as astigmatid mite-based sachets contain also food for the astigmatid mites, while in *Artemia*-based sachets, only food for the predatory mites is required) and therefore higher applicative efficiency; the simplification of sachet preparation and maintenance (as astigmatid mite-based sachets produce $CO_2$ and heat, from the prey mites and microbial activity on the bran and yeast—requiring the sachets to be made of $CO_2$-diffusing materials and making the sachets sensitive to dry conditions) and robustness of *Artemia*-based sachets with respect to sachet materials and design, transport (due to less heat production) and environmental conditions.

In various embodiments, platforms 100 as sachets may comprise *Artemia* cysts and predatory mites, possibly with carrier material and/or preservatives such as potassium sorbate or methylparaben. In certain embodiments, the sachets may comprise additional food source(s), such as astigmatid mites, pollen and/or artificially composed diets. As disclosed above, platforms 100 as sachets may comprise *Artemia* cysts externally, as feeding elements 120, to provide food for the predatory mites that leave the sachets. *Artemia* cysts may be applied directly on the outer sachet surface and/or on straps, tapes, cards or glued to threads which are attached to the sachet. For example, FIG. 4E illustrates that by applying decapsulated *Artemia* cysts externally on the sachets, a larger population of predatory mites develops outside the sachet.

In certain embodiments, combinations of different configurations of platform 100 may also be implemented (e.g., sachets and tapes).

Figure 1E:
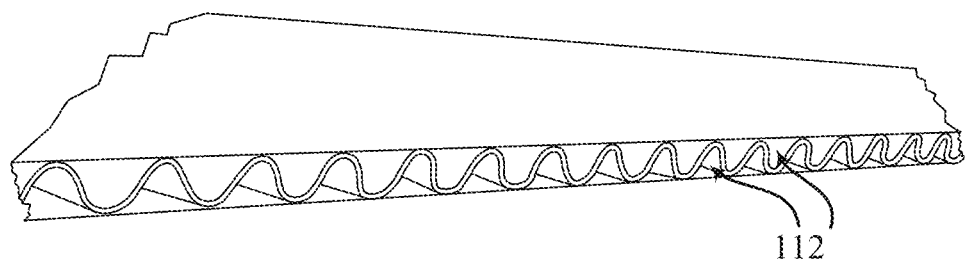
Figure 1F:
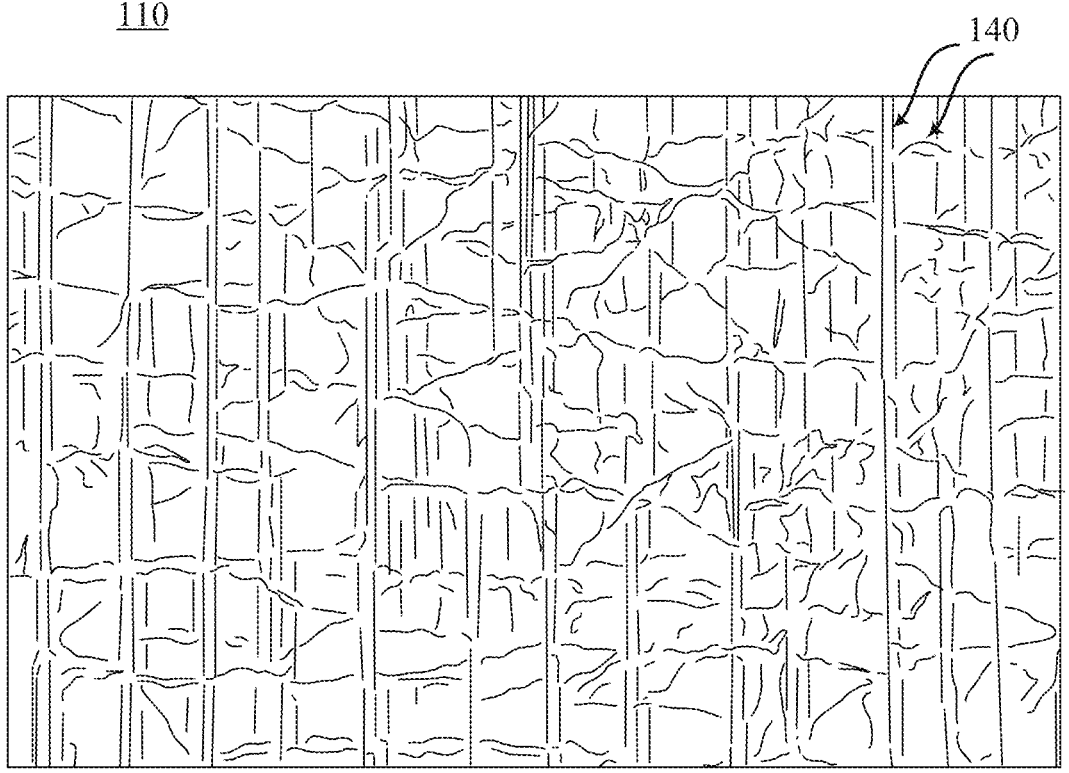

FIGS. 1E and 1F illustrate schematically mechanical supports 110 configured to provide crevices, nooks, hiding spaces, aggregation locations etc. for the natural enemies, corresponding to the preferences of the specific applied insects or mites. For example, FIG. 1E provides a schematic non-limiting example for internal spaces 112 in mechanical support 110 configured to provide aggregation locations for cryptic and/or thigmotactic-positive natural enemies such as *Orius* bugs, that may prefer a concealed and protected position on the plant, and FIG. 1F provides a schematic non-limiting example for external spaces, such as creases as surface features 140, in mechanical support 110 configured to provide staying locations for natural enemies such as mites. Either internal spaces 112 (e.g., cavities, open spaces, etc.) and/or folds, creases or other surface features 140 may be configured to provide domatia for staying and possibly reproduction of corresponding natural enemies. As noted above, platform 100 may comprise surface features 140 that comprise egg-laying (oviposition) substrate for predators that typically lay their eggs inside the plant tissue, such as predatory bugs. Such surface features 140 may be configured to provide sufficient volume and appropriate surface and material characteristics that correspond to the ovipositioning preferences of the respective predator arthropods.

In certain embodiments, feeding elements 120 may be attached or associated with internal spaces 112 and/or surface features 140, e.g. attached thereto; region 125 at least partly overlapping internal spaces 112 and/or folds, creases or other surface features 140; and/or feeding elements 120 may be at least partly filled directly onto internal spaces 112 and/or surface features 140, e.g., into internal spaces 112 which may be configured to provide unexposed reservoirs of feeding elements 120. In certain embodiments, providing feeding elements 120 in internal spaces 112 and/or surface features 140 may protect feeding elements 120 from environmental agents responsible for food quality deterioration such as water, dust and/or UV radiation—to enable even longer maintenance of the natural enemy population and/or fewer applications of platform 100 during the growth period.

Figure 1G:
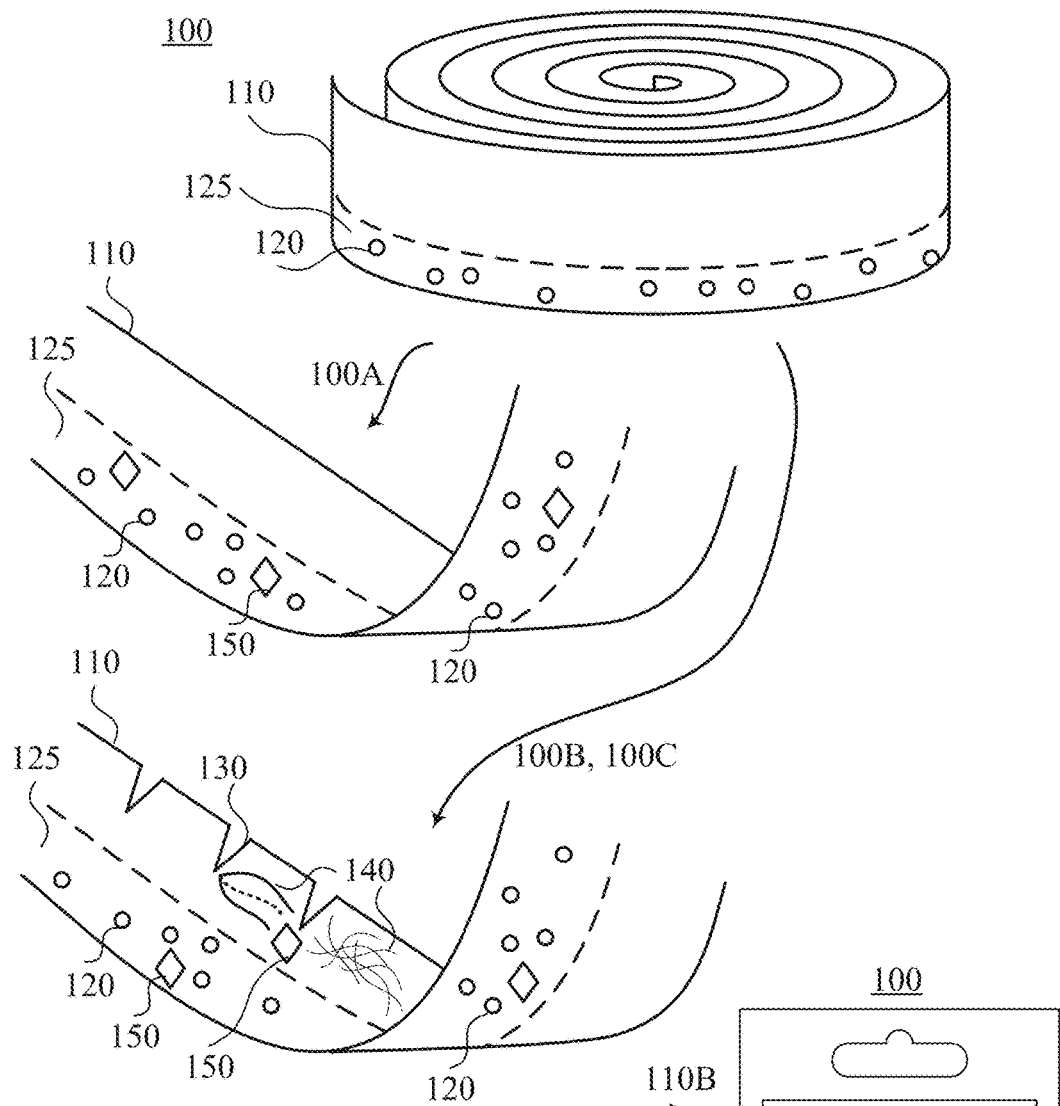
Figure 1H:
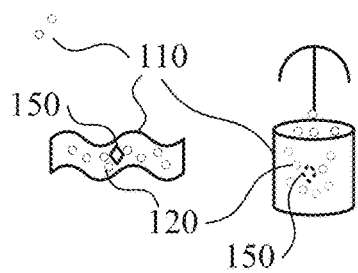
Figure 1I:
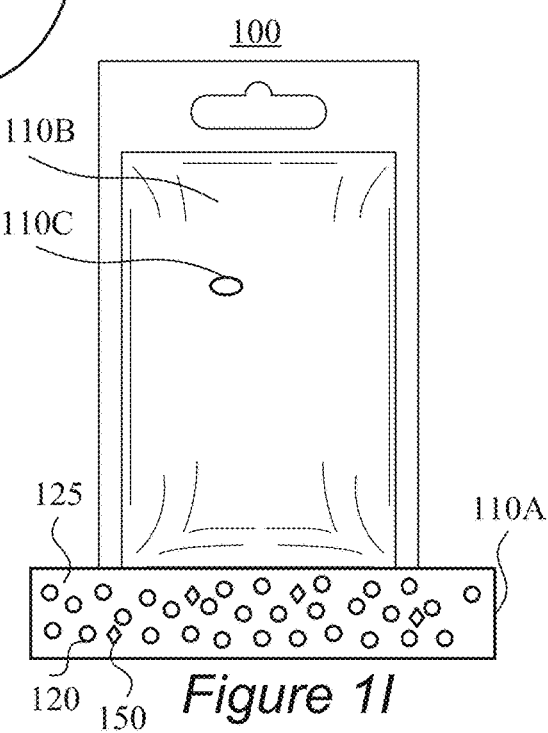

FIGS. 1G, 1H and 1I illustrate schematically platforms 100 which include early developmental stages of the natural enemies (denoted 150 and illustrated schematically) on mechanical support 110, in addition to feeding elements 120. For example, early developmental stages of the natural enemies 150 may comprise viable eggs of natural enemies, such as lacewings (Neuroptera), syrphid flies (Syrphidae, Diptera), bugs (Hemiptera), or mites (Acaridae), e.g., as provided herein. Hatching natural enemies may then feed directly on feeding elements 120 and develop on platform 100 so that platform 100 is used to both introduce (or enhance) and sustain the population of natural enemies. Specific examples for natural enemies include *Chrysoperla* lacewings, syrphid flies, as well as any of the natural enemies disclosed herein, such as predatory mites and predatory bugs. Disclosed durable *Artemia* cysts may be particularly beneficial to support hatching larvae of predatory enemies due to their long durability.

In various embodiments, natural enemies' eggs 150 may be applied to any type of disclosed platform 100, such as straps (FIG. 1G) or distributable elements (e.g., with aerial application such as by blower(s) or drone(s)) (FIG. 1H) (e.g., similar to ones illustrated in FIG. 1A) sachets (FIG. 1I and see FIG. 1D) or any other form. For example, natural enemies' eggs 150 may be attached to one or more of mechanical support(s) 110, which may comprise flat, corrugated or enclosing elements, including capsules, granules and/or particles configured to be distributed aerially and be attached to the plants upon contact. Specifically, natural enemies' eggs 150 may be applied in proximity to surface and/or volume features 140 disclosed herein (as illustrated, e.g., in FIGS. 1G, 1E, 1F) such as crevices, corrugations, internal volumes or domatia, to provide shelter and development places for the hatching larvae of natural enemies from eggs 150 as well as egg-laying places for adults coming from the environment and/or developing from eggs 150. In certain embodiments, other durable stages of natural enemies may be associated with platform 100 such as pupae or even larvae or adults which may be added upon application of platform 100. Natural enemies may be added to any of the platform embodiments disclosed herein.

Figure 7A:
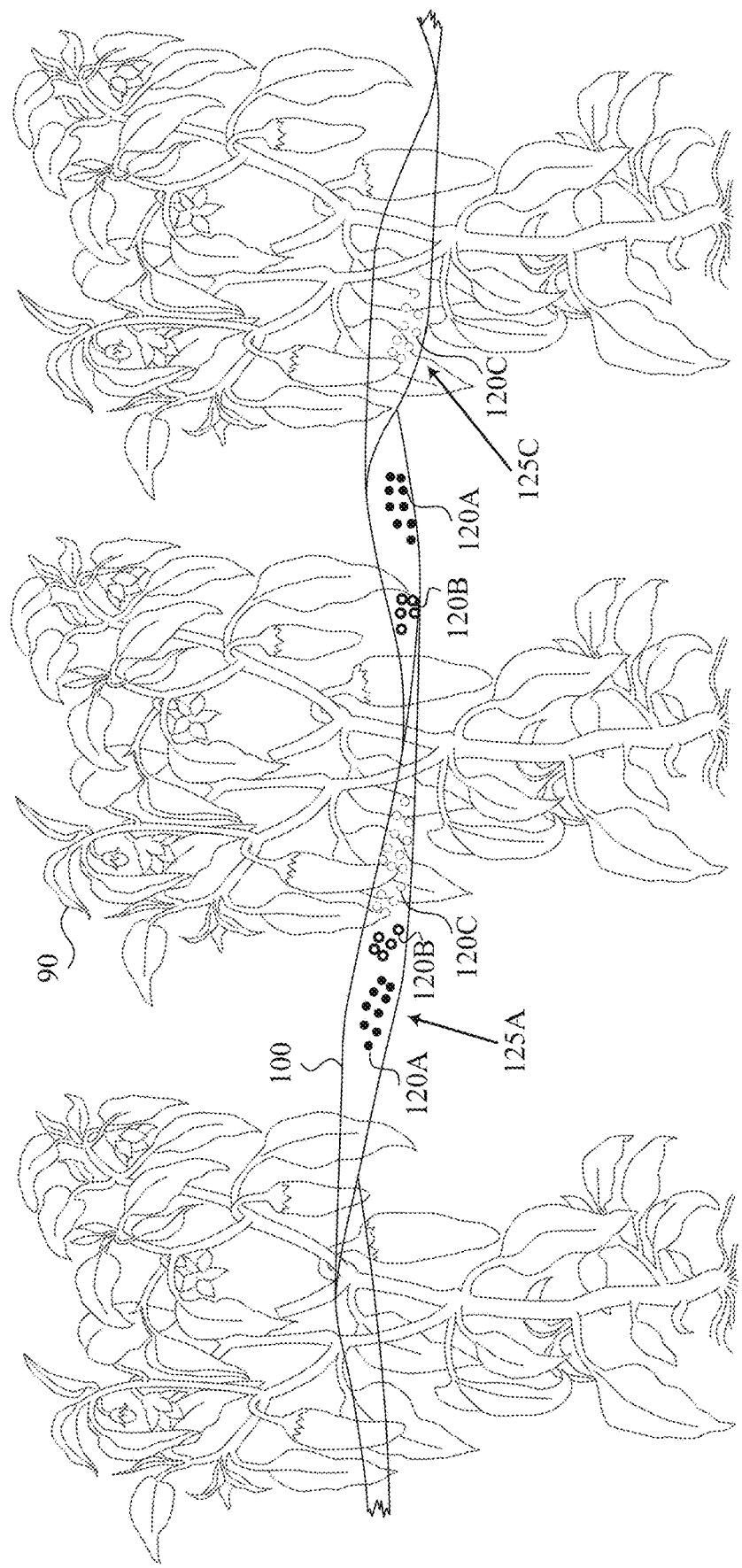
FIG. 7A is a high-level schematic illustration of monitoring the population of natural enemies on plants using platform, according to some embodiments of the invention.

Advantageously, disclosed platforms 100 provide continuous supply of feeding elements 120 both (i) spatially over a large expanse of the crop plants, e.g., over horizontal and/or vertical linear platforms spanning at least one spatial dimension of the crop—providing feeding elements in relative proximity to the natural enemies over the whole volume of the crop plants; and (ii) temporally over most or all of the growth period due to multiple applications of platform 100 and/or due to the very long freshness (effectiveness as feed) duration and post-application durability of feeding elements 120 resulting from the disclosed configurations—e.g., the preparation method of feeding elements 120, optional use of carrier material that is pretreated with preservatives (e.g., sand, sawdust, plant material etc.), the protection of at least some of feeding elements 120 from adverse environmental factors (water, dust, UV radiation), and the large spatial spreading of feeding elements 120 ensuring availability after initial feeding (see the monitoring method and FIG. 7A below).

For example, prior art cards providing *Ephestia* eggs provide the eggs only for a short period before they become unsuitable as food (typically few days) and only in a patchy and isolated spatial distribution. In contrast, disclosed platforms 100 provide long lasting feeding elements 120 which are effective as feed at least for ten weeks, as shown below in experimental results; and spatially distributed over a large portion of the crop, typically covering at least one spatial direction (e.g., width and/or height) of the whole crop. Moreover, disclosed solutions and platforms 100 are applicable to a wide range of natural enemies and crops, and are generic in nature.

In certain embodiments, platform 100 may further comprise visual indicators (not shown) associated with feeding elements 120 such as general color of mechanical support 110, color pattern(s) and/or marks thereupon which indicate the presence and/or the location of regions 125 and/or feeding elements 120. For example, visual indicators may comprise a yellow color of mechanical support 110 and/or the vicinity of feeding elements 120 (e.g., region 125), a color pattern which emphasizes feeding elements 120 or their vicinity (e.g., by creating an appropriate color contrast with the surroundings), or any other type of indicator which may promote the predators learning of the provided food source. Visual indicators may be used in any of the disclosed configurations of platform 100.

In certain embodiments, platform 100 may further comprise olfactory cues associated with platform 100 and/or indicating feeding elements 120, which enhance the efficiency of the natural enemies finding feeding elements 120 (see, e.g., Janssen et al. 2014, Time scales of associating food and odor by predator communities in the field, Behavioral Ecology 25, 5: 1123-1130—for field studies). For example, various artificial or natural odor sources may be attached to mechanical support 110 to facilitate learning and improved response by both predatory bugs and mites. Examples for applied odors may comprise one or more volatile compounds such as plant oils (mint oil, *eucalyptus* oil etc.) or one or more mixes of compounds such as any of menthol, menthone, (+)-menthyl acetate, menthofuran, isomenthone, limonene, 1,8-cineole etc. It is noted that olfactory cues may be learned by the predators and associated with the presence of feeding elements 120, making many odors applicable, as long as they are not harmful to the respective predators. Olfactory cues may be used in any of the disclosed configurations of platform 100.

Elements from configurations 100A-D may be combined in any operable combination, and the illustration of certain elements in certain configurations and not in others merely serves an explanatory purpose and is non-limiting.

Figure 2:
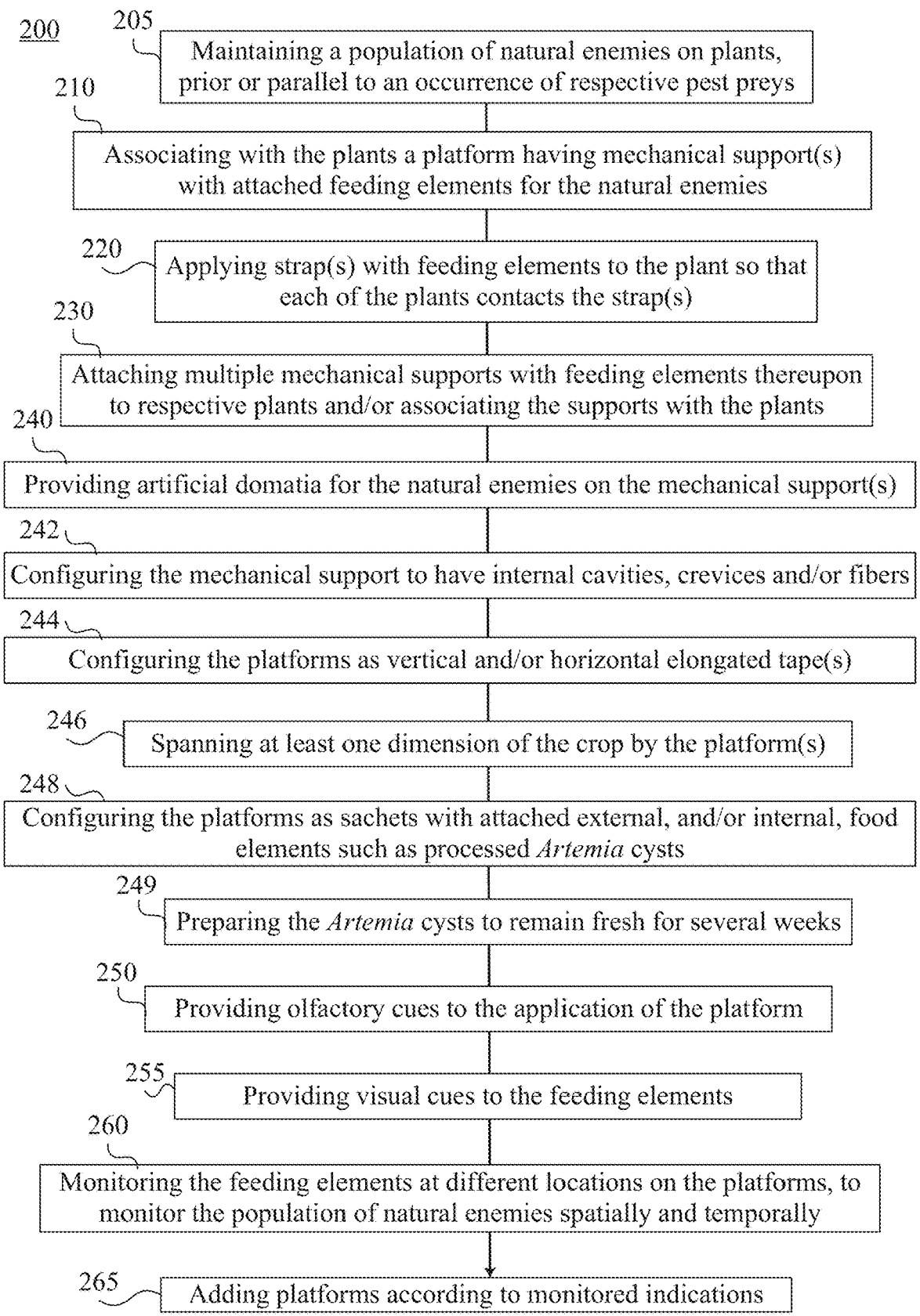
FIG. 2 is a high-level flowchart illustrating a method, according to some embodiments of the invention.

FIG. 2 is a high-level flowchart illustrating a method 200, according to some embodiments of the invention. The method stages may be carried out with respect to platform 100 described above, which may optionally be configured to implement method 200. Method 200 may comprise the following stages, irrespective of their order.

Method 200 comprises maintaining a population of natural enemies on plants, prior or parallel to an occurrence of respective prey pests (stage 205) by associating with the plants a platform comprising at least mechanical support with attached feeding elements for the natural enemies (stage 210).

The mechanical support may comprise one or more straps, and method 200 may further comprise applying the strap(s) to the plant so that each of the plants contacts the strap (stage 220). The strap may comprise feeding elements attached on one or both sides of the strap, e.g., to adhesive strip(s) along the one or both sides of the strap.

The platform may comprise multiple mechanical supports with attached feeding elements, and method 200 may further comprise applying, associating, attaching or affixing the mechanical supports to respective plants (stage 230), e.g., by directly attaching the mechanical supports to respective plants, by spreading multiple mechanical supports above the plants and letting them fall and entangle in the plants, or by other association means.

In certain embodiments, method 200 may comprise providing, on the mechanical support(s), artificial domatia and/or oviposition substrate for the natural enemies (stage 240) such as hairs or cavities for shelter and possibly for laying eggs.

In certain embodiments, method 200 may comprise configuring the mechanical support to have internal cavities, crevices and/or fibers (stage 242). method 200 may comprise configuring the platforms as vertical and/or horizontal elongated tape(s) (stage 244) and spanning at least one dimension of the crop by the platform(s) (stage 246).

In certain embodiments, method 200 may comprise configuring the platforms as sachets with attached external, and/or internal, food elements such as processed *Artemia* cysts (stage 248). Certain embodiments may comprise the preparation of the *Artemia* cysts to remain effective for several weeks, e.g., at least three, four, seven or more weeks, depending on environmental conditions (stage 249).

In certain embodiments, method 200 may further comprise providing olfactory cues to the application of the strap (stage 250). In certain embodiments, method 200 may further providing visual cues to the feeding elements (stage 255).

In certain embodiments, method 200 may further comprise monitoring the feeding elements (e.g., color of cysts) at different locations on the platforms, to monitor the population of natural enemies spatially and temporally (stage 260) and possibly adding platforms according to monitored indications (stage 265).

In certain embodiments, method 200 and platforms 100 may be applied at an early stage of crop production, possibly already at the plant nursery.

Figure 3A:
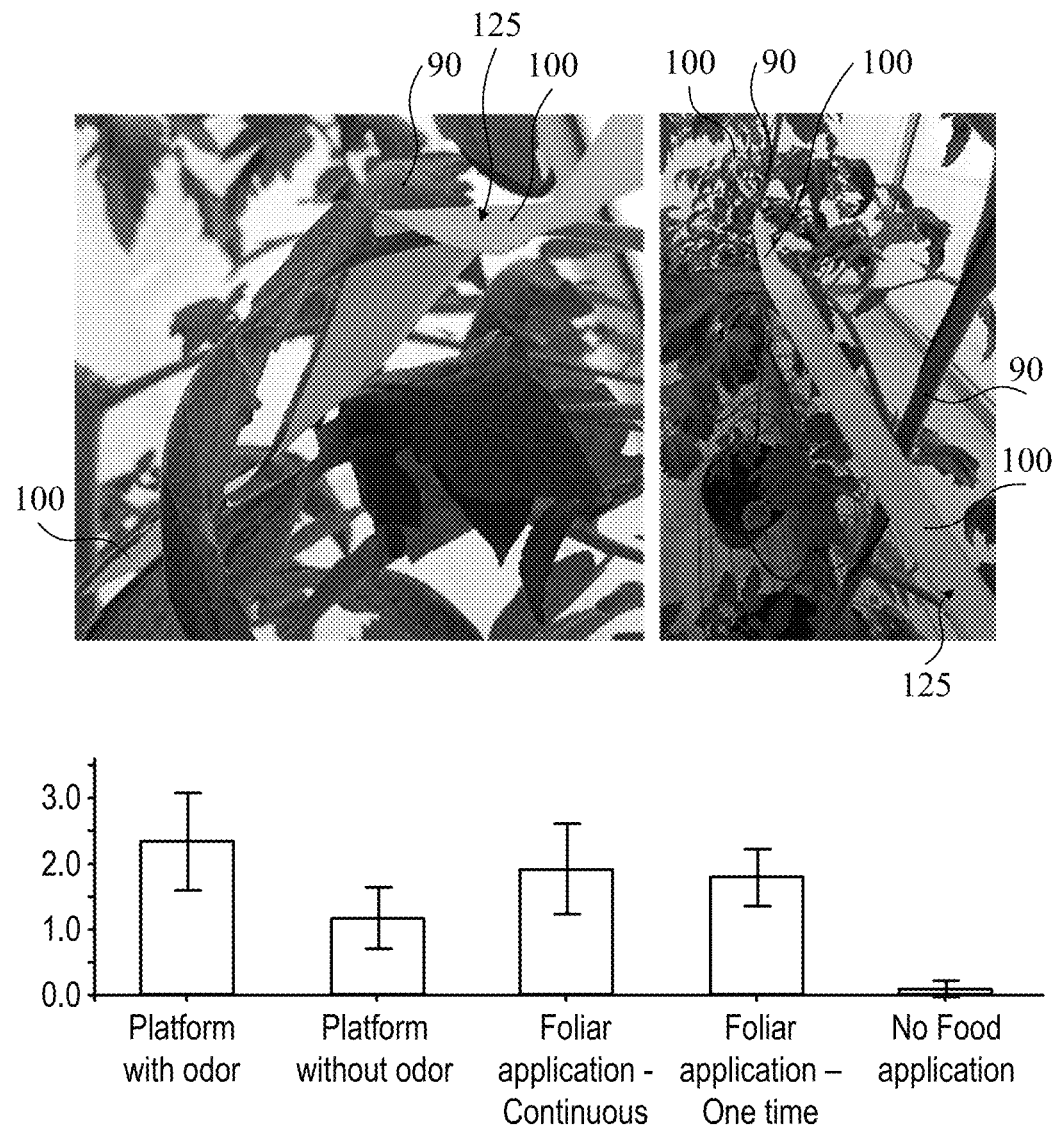
FIGS. 3A-3E provide initial, non-limiting, experimental evidence for the efficiency of the methods of applying platforms, according to some embodiments of the invention.
Figure 3B:
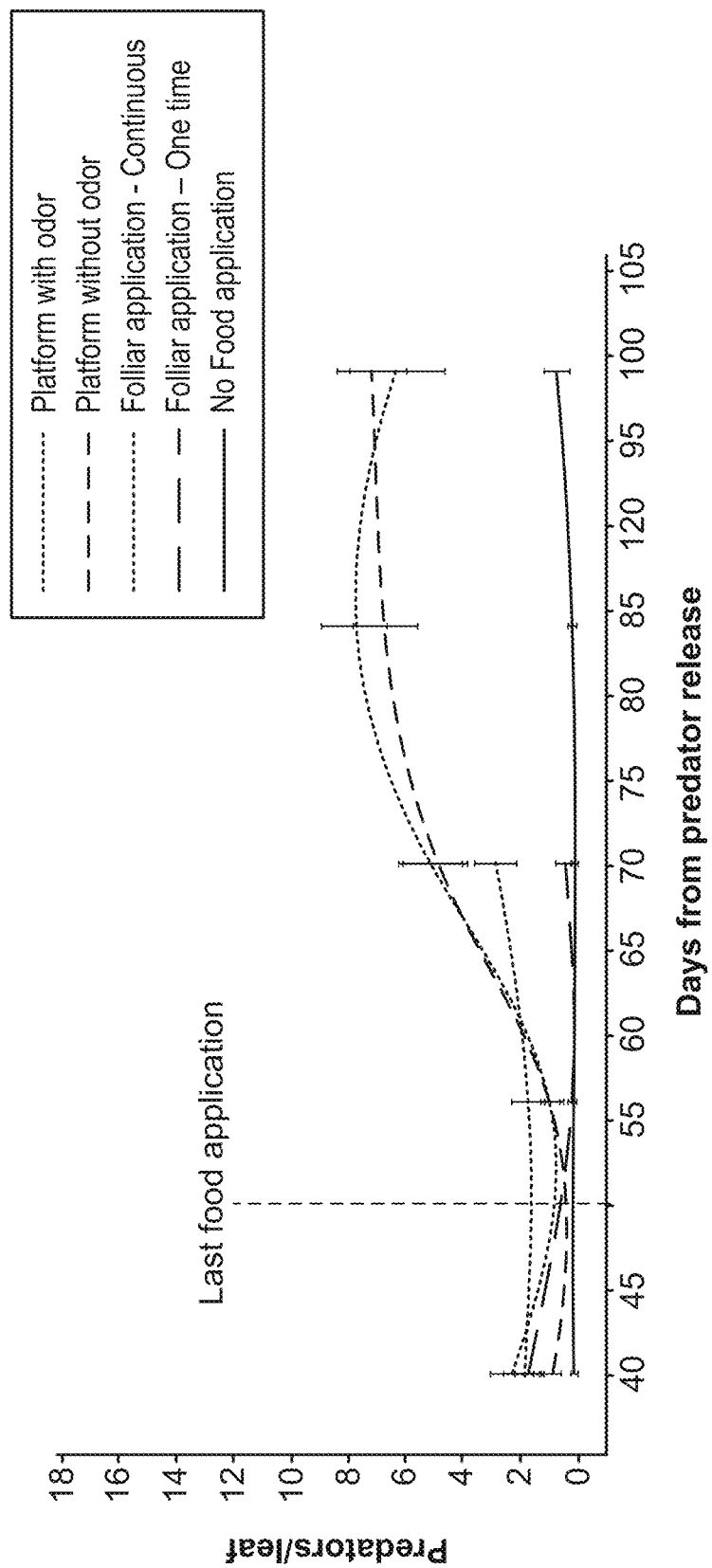
Figure 3C:
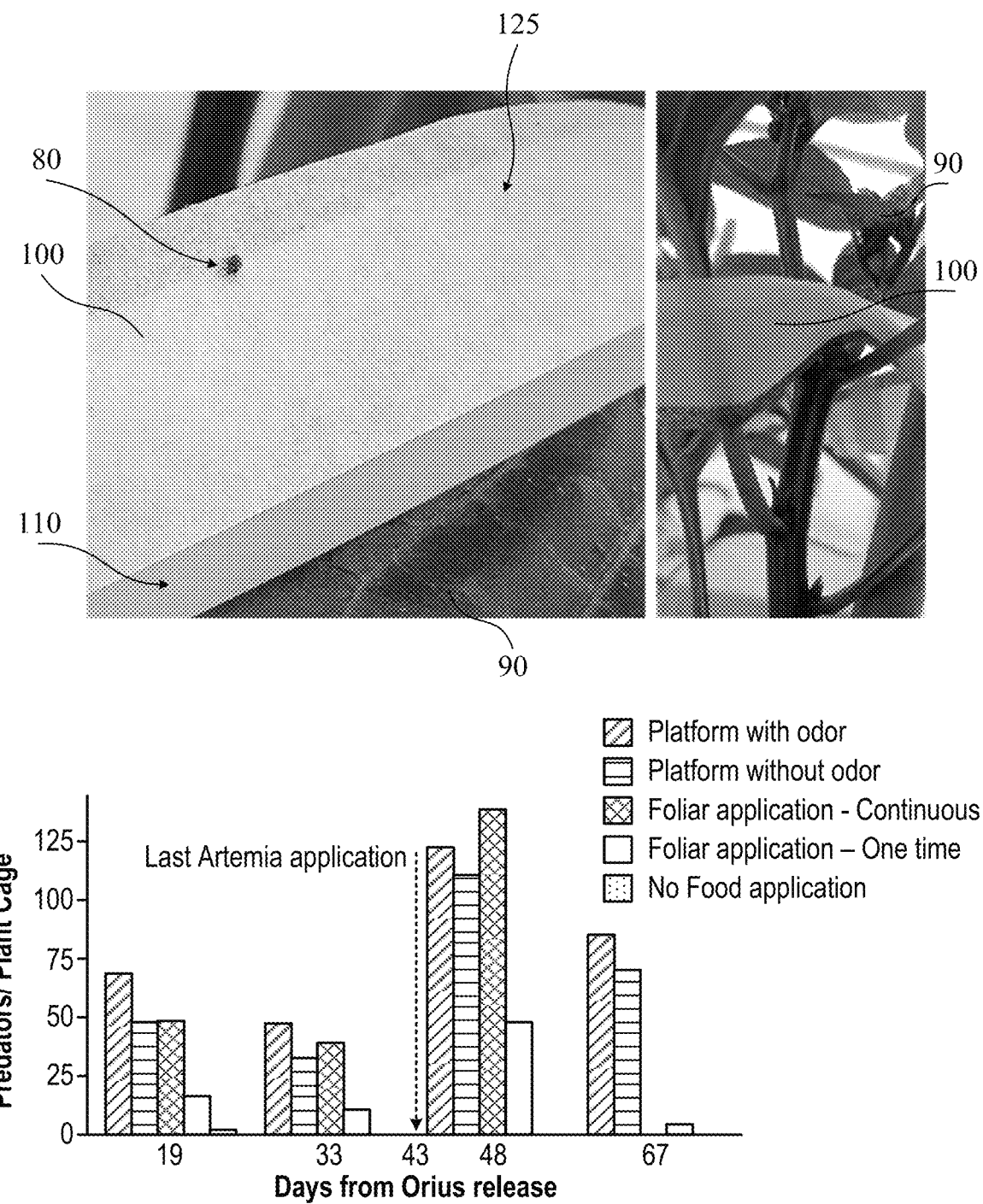
Figure 3D:
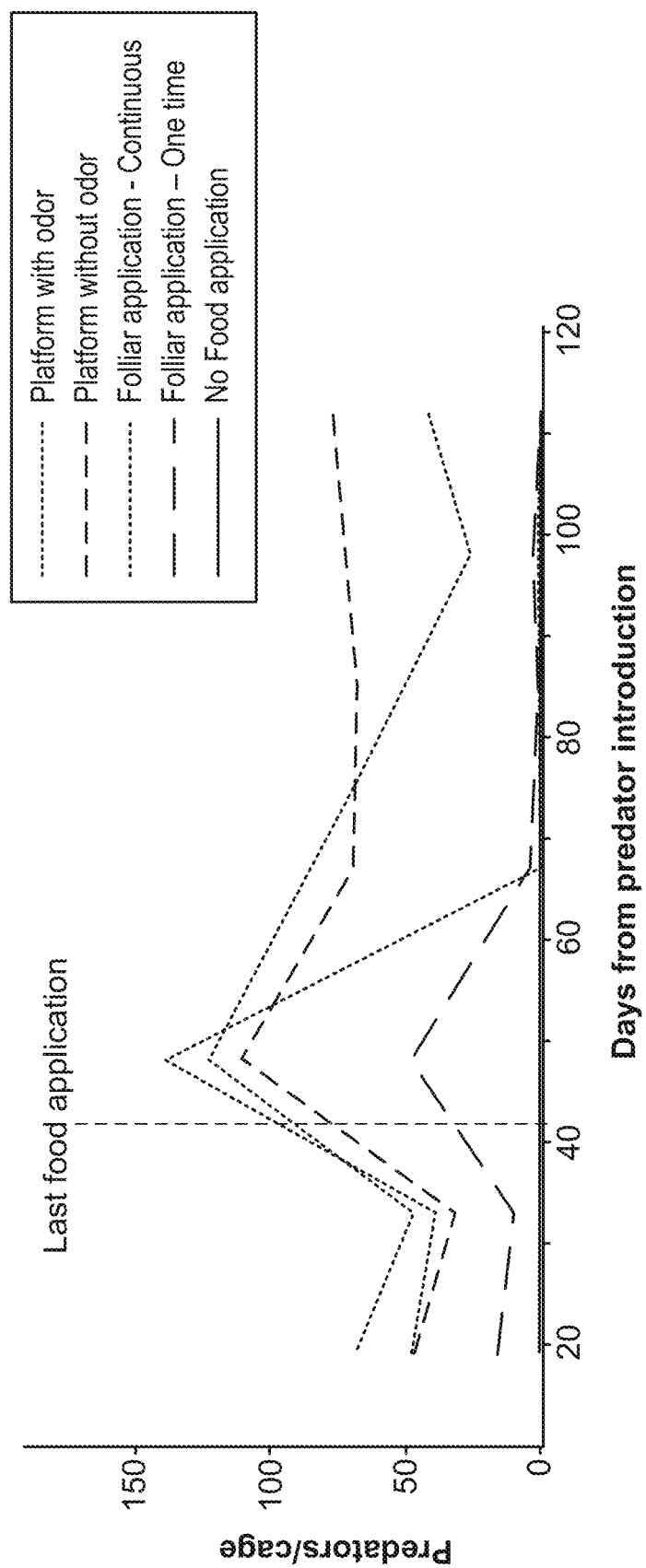
Figure 3E:
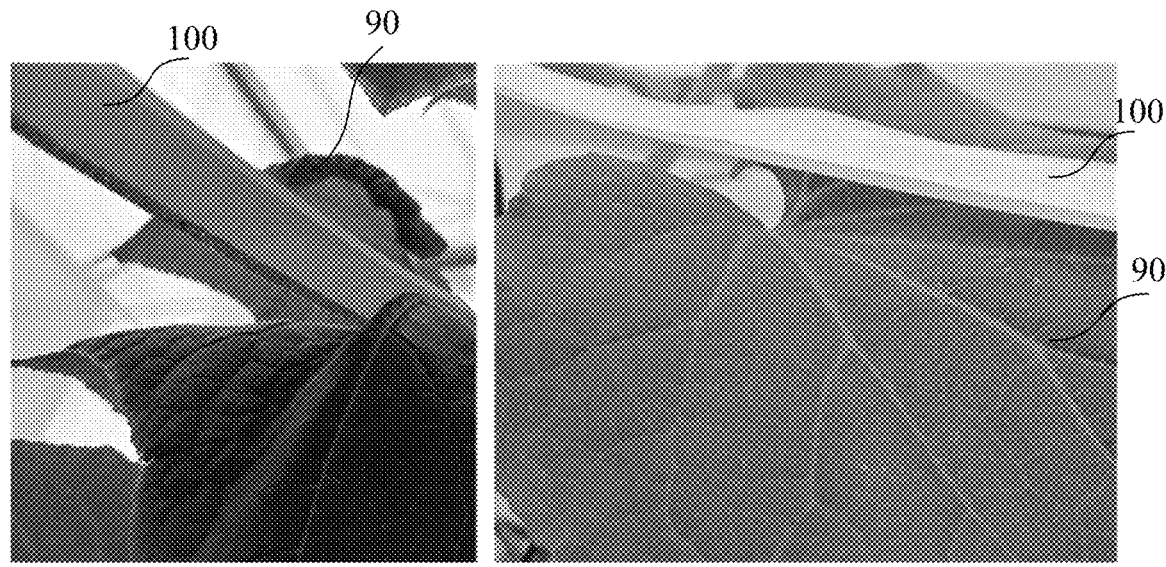
Figure 3E:
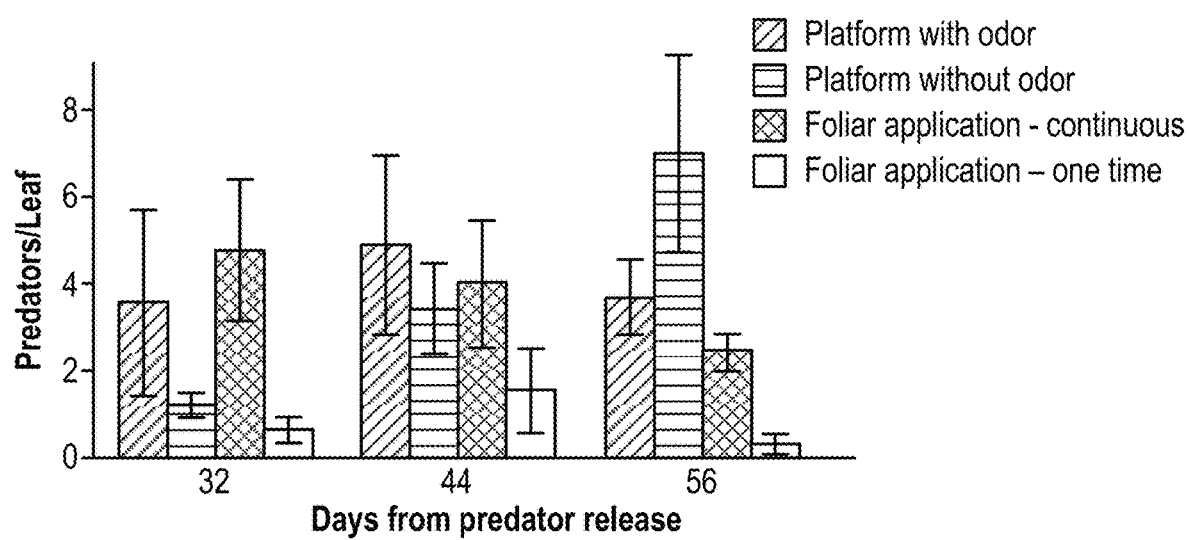

FIGS. 3A-E provide initial, non-limiting, experimental evidence for the efficiency of methods 200 and applying platforms 100, according to some embodiments of the invention. In the non-limiting examples, processed *Artemia* cysts were used as feeding elements 120 in the presented pilot trials. Each of FIGS. 3A, 3C and 3E illustrates in photos the application of platform 100 with strap mechanical supports 110 having adhesive strips with feeding elements 120 on one side, as a non-limiting example, and respective graphs illustrating the efficiency of application of platform 100 with respect to prior art methods. FIGS. 3A-E provide data relating to three key generalist predators from different taxa on three important crops, for applying platform 100 (once in two weeks) with and without odor (olfactory cues) with respect to continuous (once in two weeks) and one-time foliar application (as prior art methods) and no food application.

FIGS. 3A and 3B relate to the application of the predatory bug *Macrolophus pygmeus* (Heteroptera: Miridae) on tomato as plant 90, the data in FIG. 3A was collected 40 days after predator release, while the data in FIG. 3B was collected 100 days after predator release. When food is applied once in two weeks, both platform applications are effective (with respect to no feed application) and comparable with foliar application with respect to the predator establishment. However, 20 days after the last food application, predator population are higher on the platform application than on the conventional foliar application. The platform maintains predator populations high for a period of at least 50 days after the last food application. Prior art feeding intervals are 7-14 days, hence the platform is better with respect to ease of use, durability post application, and efficiency. In this experiment, the amount of food per application is similar between treatments. It is noted that the standard error is calculated for among leaves in the same and only replicate of the pilot (pseudoreplicates).

FIGS. 3C and 3D relate to the application of the predatory bug *Orius laevigatus* (Heteroptera: Anthocoridae)—one of which indicated by numeral 80 in the image—on sweet pepper as plant 90, food (*Artemia* processed cysts) was applied every 14 days until day 43 to plant cages containing five plants each (platform 100 was provided as fresh tapes every 14 days). The data in FIG. 3C was collected 67 days after predator release, while the data in FIG. 3D was collected 110 days after predator release. As illustrated in FIG. 3C, as food application continues, predator establishment is similar on plants treated with platform 100, and on plants with continuous foliar application of *Artemia*. However, as illustrated in FIGS. 3C and 3D, when food application stops (indicated as "last *Artemia* application"), predator population crashed on the foliar application treatments, but remained high on plants treated according to method 200 with platform 100 for a period of 70 days after the last food application. This indicates longer durability of food when using the disclosed treatment as compared to prior art methods, which require a 7-14 days feeding interval. It is noted that the number of predators per cage is slightly higher on the platform 100 with odor embodiment, indicating odor addition may improve predator establishment.

FIG. 3E relates to the application of the predatory mite *Amblyseius swirskii* (Arachnida: Mesostigmata: Phytoseiidae) on cucumber as plant 90, indicating the high efficiency of platforms 100 and methods 200 which is comparable and even superior to prior art methods in the long run.

It is noted that the examples presented in FIGS. 3A-E show that *Artemia* cysts, prepared as disclosed herein, last as feeding elements 120 from at least seven to ten weeks, which is an order of magnitude longer than prior art feeding elements. It is further noted that *Artemia* cysts, prepared as disclosed herein, have also been applied to flowers (*chrysanthemum*) crops and have been shown to keep their freshness and usability as feeding elements in experimental massive foliar application.

FIGS. 4A-E, 5A and 5B provide additional experimental results that illustrate the effectiveness and advantages of platforms 100 and methods 200, according to some embodiments of the invention.

Figure 4A:
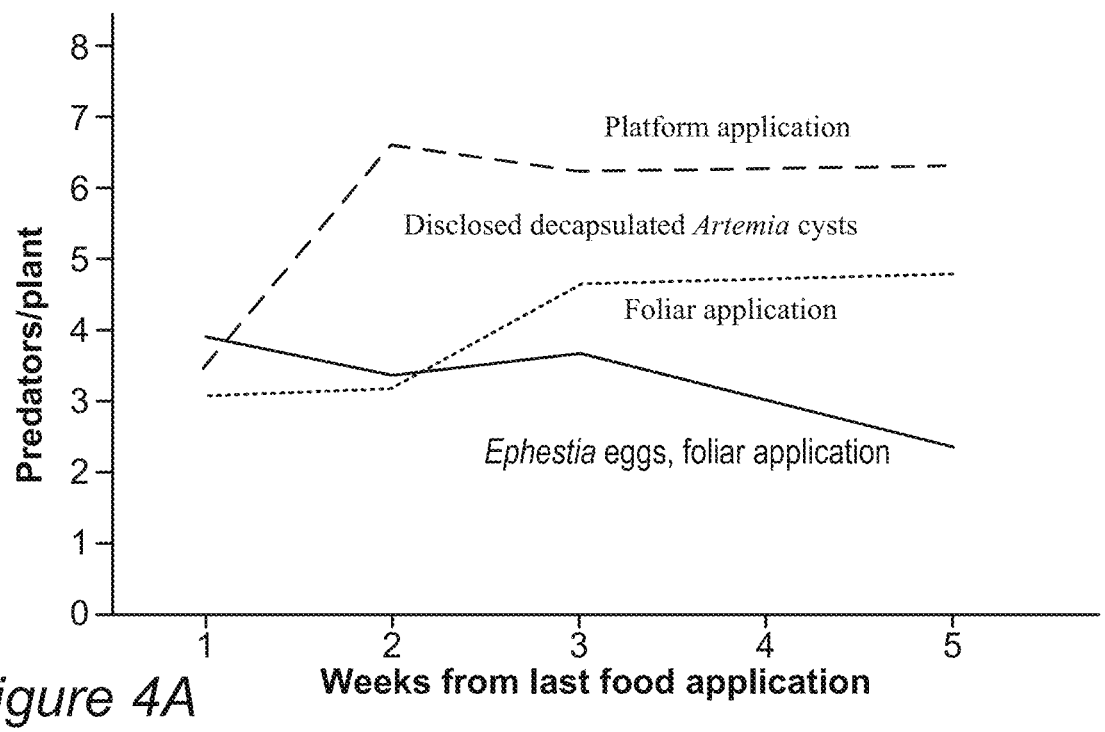
FIGS. 4A-E, 5A and 5B provide additional experimental results that illustrate the effectiveness and advantages of the platforms and the methods, according to some embodiments of the invention.

FIG. 4A provides experimental evidence for the effect of feed type and feed application method on populations of *Orius laevigatus* on pepper, comparing decapsulated *Artemia* cysts (see e.g., method 249 below) applied in foliar application and applied using platform 100, according to some embodiments of the invention—with the standard feeding with *Ephestia* eggs, which is currently the only available high-quality feed for *Orius* bugs on crops. The required application frequency of *Ephestia* eggs is once per week, because of the limited durability of this feed. In contrast, disclosed decapsulated *Artemia* cysts, as described below, provide a much longer feed viability and corresponding much lower required feeding frequency. FIG. 4A illustrates the development of *Orius laevigatus* populations on sweet pepper, after the weekly feed application was stopped (at week "0, it is noted that the population fed on *Ephestia* eggs did not collapse due an experimental artefact). The results illustrate that disclosed decapsulated *Artemia* cysts support the *Orius* populations in either application method similarly to *Ephestia* eggs during feeding, and that the *Orius* population is maintained better on disclosed decapsulated *Artemia* cysts than on *Ephestia* eggs feed after feeding is stopped, probably due to the higher durability of the feed, providing sufficient rudimentary feed source. Moreover, application of disclosed decapsulated *Artemia* cysts on platforms 100 was shown to further improve *Orius* population levels, beyond standard foliar application, possibly due to the even higher durability of feed on platforms 100.

Figure 4B:
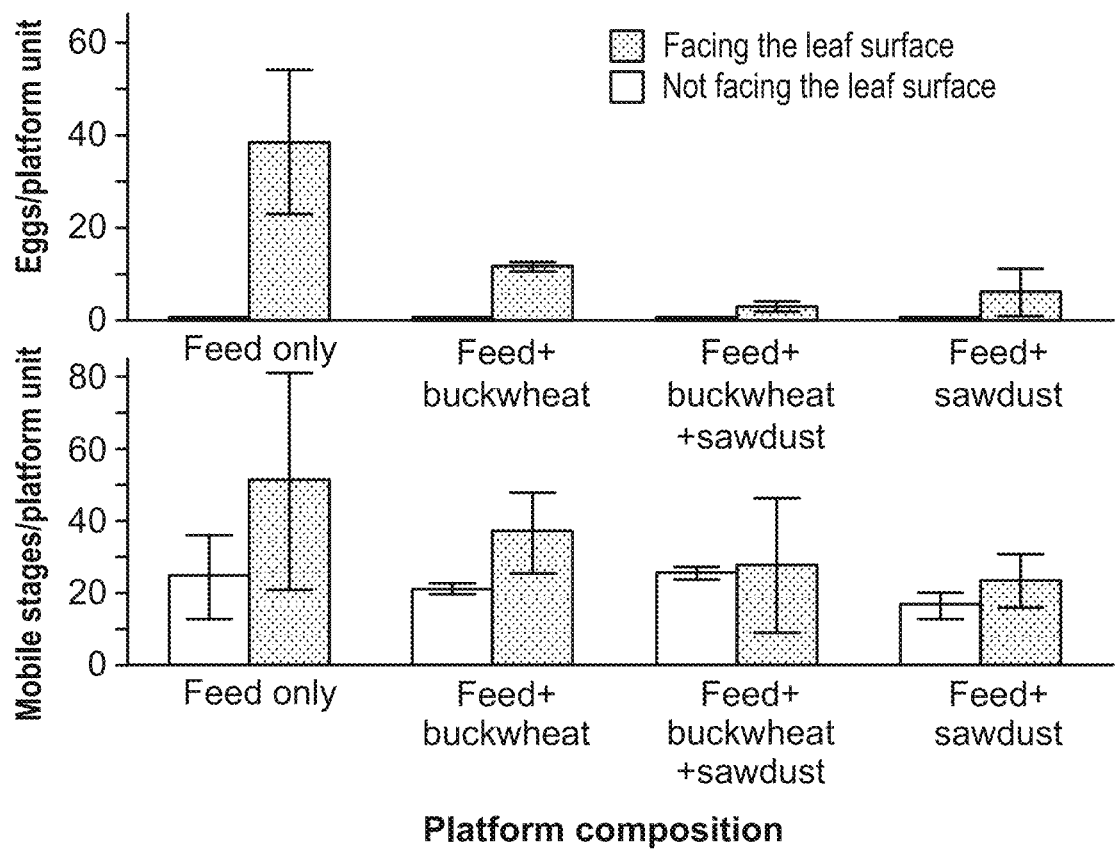

FIG. 4B provides experimental evidence for the oviposition substrates provided by platforms 100 for predatory mites, illustrating that platforms 100 and methods 200, according to some embodiments of the invention, provide shelters and oviposition substrate to predatory arthropods, in addition to providing them with feed (see, e.g., FIGS. 1E and 1F as non-limiting examples). FIG. 4B illustrates results concerning the response of *Amblyseius swirskii* to platform units 100 having sizes of 2×2 $cm^2$ (see e.g., FIG. 1A with various small-structure embodiments of platform 100, other than straps) on cucumber leaves. Feed was applied with or without additives on both sides of platforms 100. The presence of predatory mites (mobile stages) and eggs separately were measured separately, on both sides of the platform. *Amblyseius swirskii* formed colonies on all tested varieties of platform 100. Mobile stages were present on both sides of platform 100, while eggs were oviposited only on the surface of platform 100 that was facing the leaf area, e.g., protected from radiation. The trial shows that the platform indeed provides shelter and oviposition substrate to *A. swirskii*, independent of the presence of additives or carriers (e.g., sawdust or buckwheat hulls (*Fagopyrum esculentum*) as plant material on platform 100.

Figure 4C:
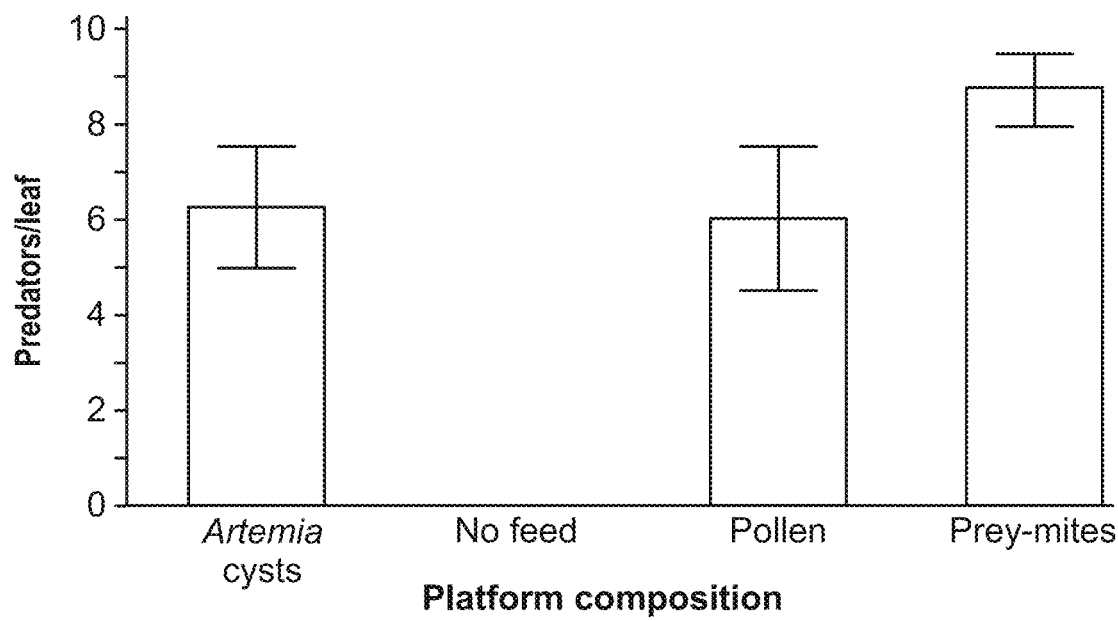

FIG. 4C provides experimental evidence that platform 100 can be applied with various foods as feeding elements 120, such as disclosed *Artemia* cysts, pollen (of *Typha latifolia*) and/or prey mites and/or diets for prey mites—according to some embodiments of the invention. For example, *Amblyseius swirskii* predator populations on cucumber were successfully supported by the three different illustrated feed types on platforms 100. The fed prey mites were mites from the Astigmata group, normally used in predatory-mite mass rearing. There are many species of prey mites and prey-mite diets that may be used. In this non-limiting example, *Carpoglyphus lactis* eggs were used in combination with a yeast-wheat germ-bran-based diet for the prey mites, to allow for a prey population to develop on platform 100, and thus continue to produce more feed for the predators than the amount introduced to start with. All the platform varieties tested in this trial resulted in higher predator numbers on the crop, compared to a control where no feed was applied.

Figure 4D:
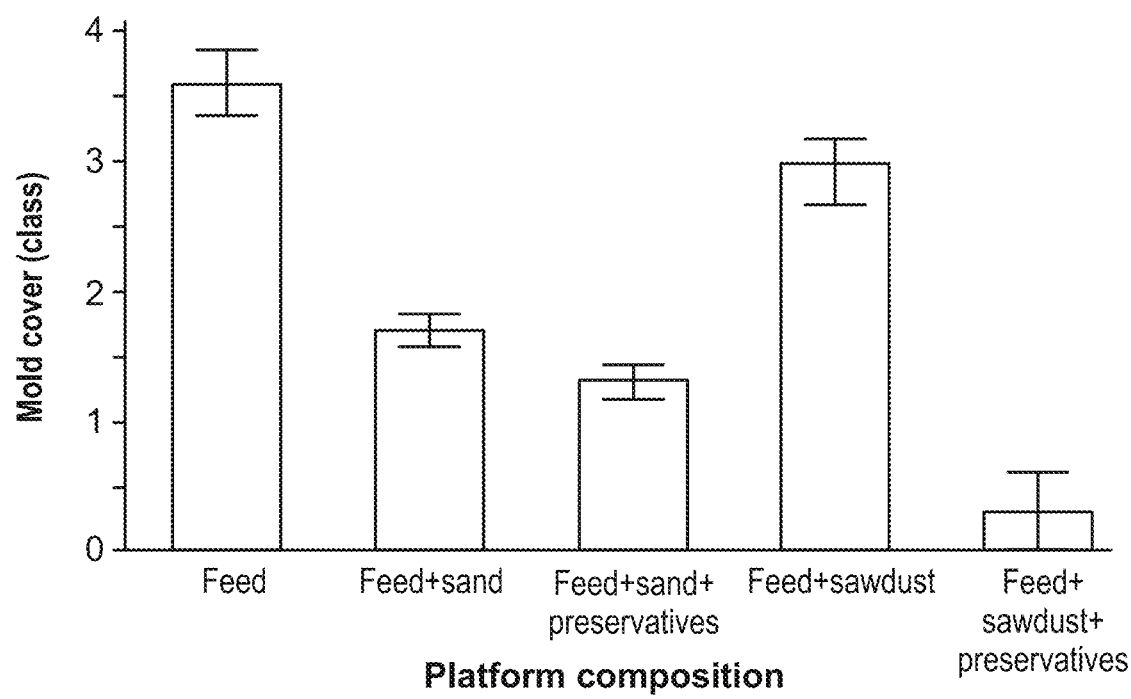
Figure 4E:
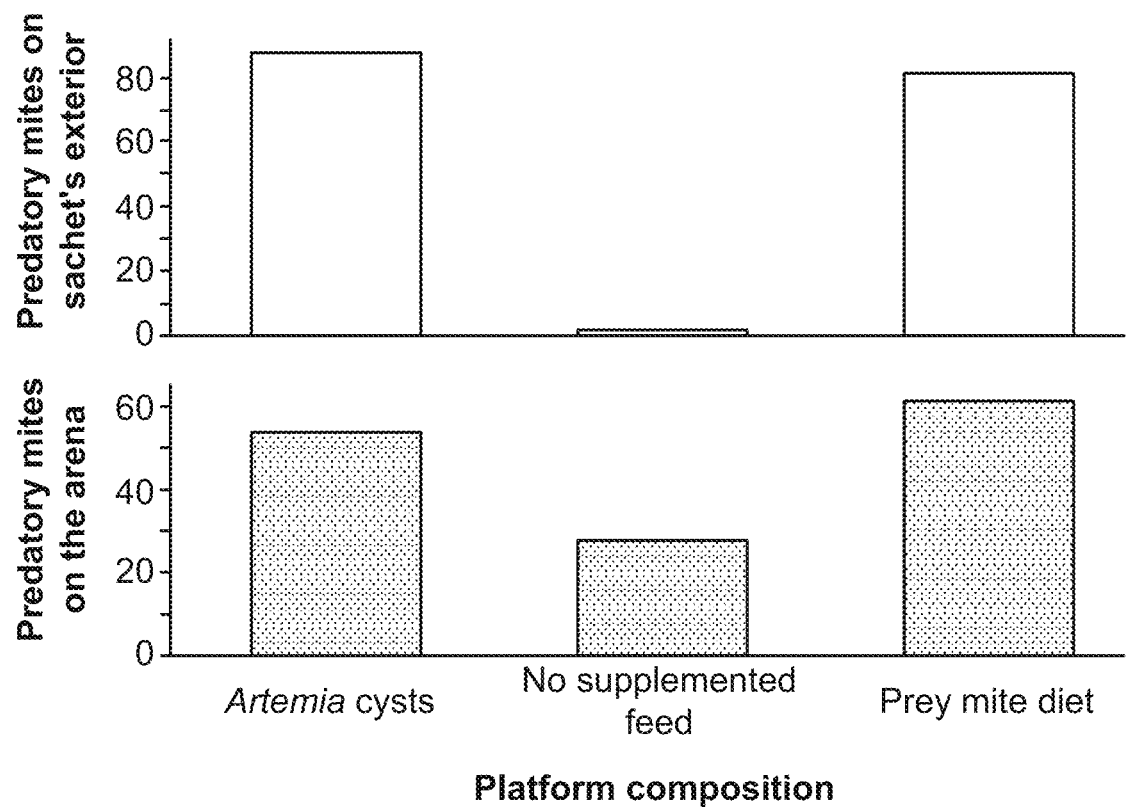

FIG. 4D provides experimental data concerning the effect of the composition of platform 100 on mold development rate on feeding elements 120, according to some embodiments of the invention. Besides feeding elements 120, additives such as granular and/or absorbent material (e.g., sand, sawdust, plant material) and/or preservatives may be applied on platform 100 to provide shelters and oviposition substrate (see e.g., FIGS. 4B and 4C) and/or enhance the durability of feeding elements 120. As illustrated in FIG. 4D, application of feeding elements 120 together with additives on platform 100 resulted in a lower development rate of mold on feeding elements 120, particularly when the additives were treated with preservatives (see also below, concerning preservatives used in the preparation of decapsulated *Artemia* cysts).

FIG. 4E provides experimental data concerning the effect of adding feeding elements 120 externally to platforms 100 configured as sachets (see, e.g., FIG. 1D and related description), according to some embodiments of the invention. A popular way to apply predatory mites on crops is in sachets that contain a breeding colony of predatory mites and prey mites. These sachets typically release prey and predatory mites to the crop for a period of four to six weeks. Certain embodiments comprise adding decapsulated *Artemia* cysts inside and/or outside platforms 100 configured as sachets may yield higher numbers of predators and provide them for a longer period of time than in the prior art, e.g., due to the long durability of decapsulated *Artemia* cysts that is shown below. In certain embodiments, additional feeding elements 120 may be provided as food sources on the exterior of platforms 100 configured as sachets, such as food for the prey-mites that leave the sachet (see e.g., FIG. 4D). Possibly, adding feeding elements 120 for the prey mites on the exterior of platforms 100 configured as sachets may allow them to establish populations and reproduce also outside the sachets. Such a population of prey-mites on the exterior of the sachet may be exploited by the predatory mites that come out of the sachet and help them to establish on the crop. FIG. 4E demonstrates that supplementing feed on the outer surface of the sachets can increase predator numbers outside the sachet. In the example *Amblyseius swirskii* sachets were supplemented with *Artemia* cysts (inside and outside the sachet) or with a bran-yeast based diet for the prey mite *Carpoglyphus lactis*. The sachets were positioned on arenas and compared to *A. swriskii* sachets without any supplemented feed. The numbers of *A. swirskii* on the sachet's exterior and on the arena were counted 24 days later and illustrate larger populations than when used without supplemental feeding elements 120.

Figure 5A:
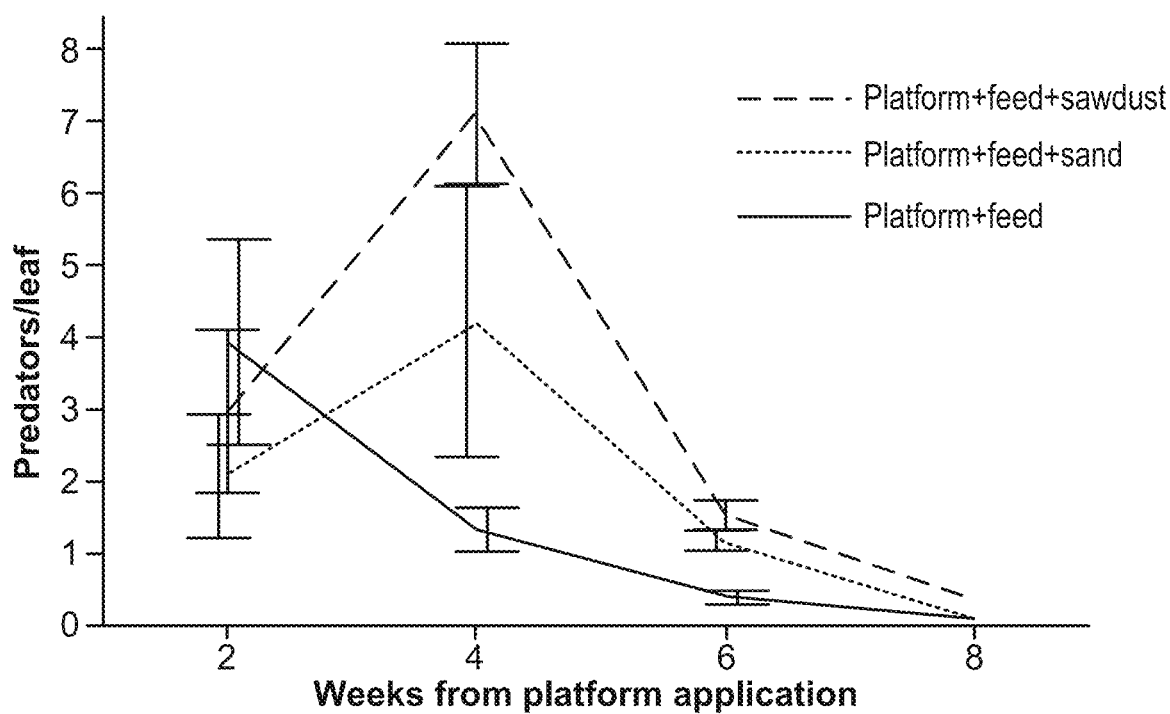
Figure 5B:
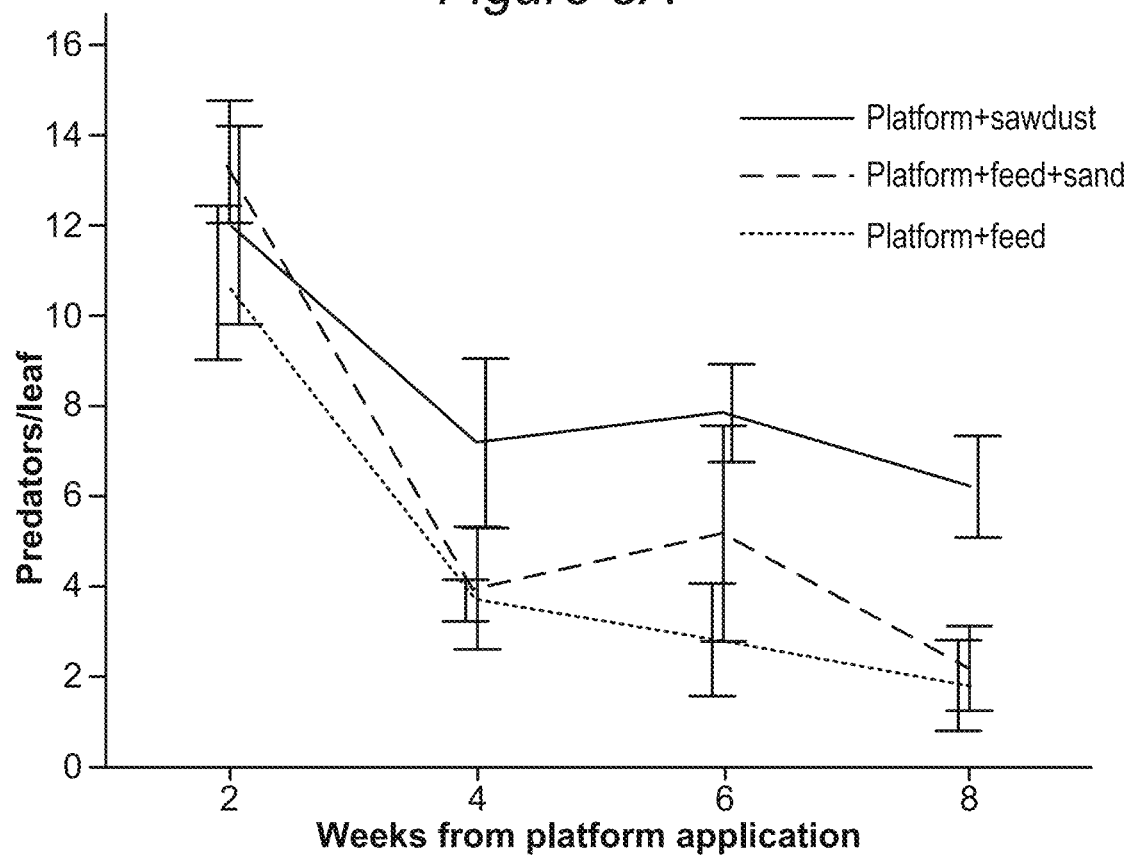

FIGS. 5A and 5B provide experimental data that demonstrate that platforms 100 comprising a combination of feed and preservative-treated additives supported predator populations on the crop for a longer period than platforms 100 with feed alone, according to some embodiments of the invention. FIGS. 5A and 5B provide experimental data concerning the effects of platform composition on *Orius laevigatus* populations on sweet-pepper (in cages containing several plants, termed semi-field conditions) and on *Macrolophus pygmeus* populations on tomato (similarly, under semi-field conditions), respectively, and show that in certain embodiments, additions of carrier material and/or preservatives increase the efficiency of platforms 100 in supporting the populations of predatory arthropods.

Figure 6A:
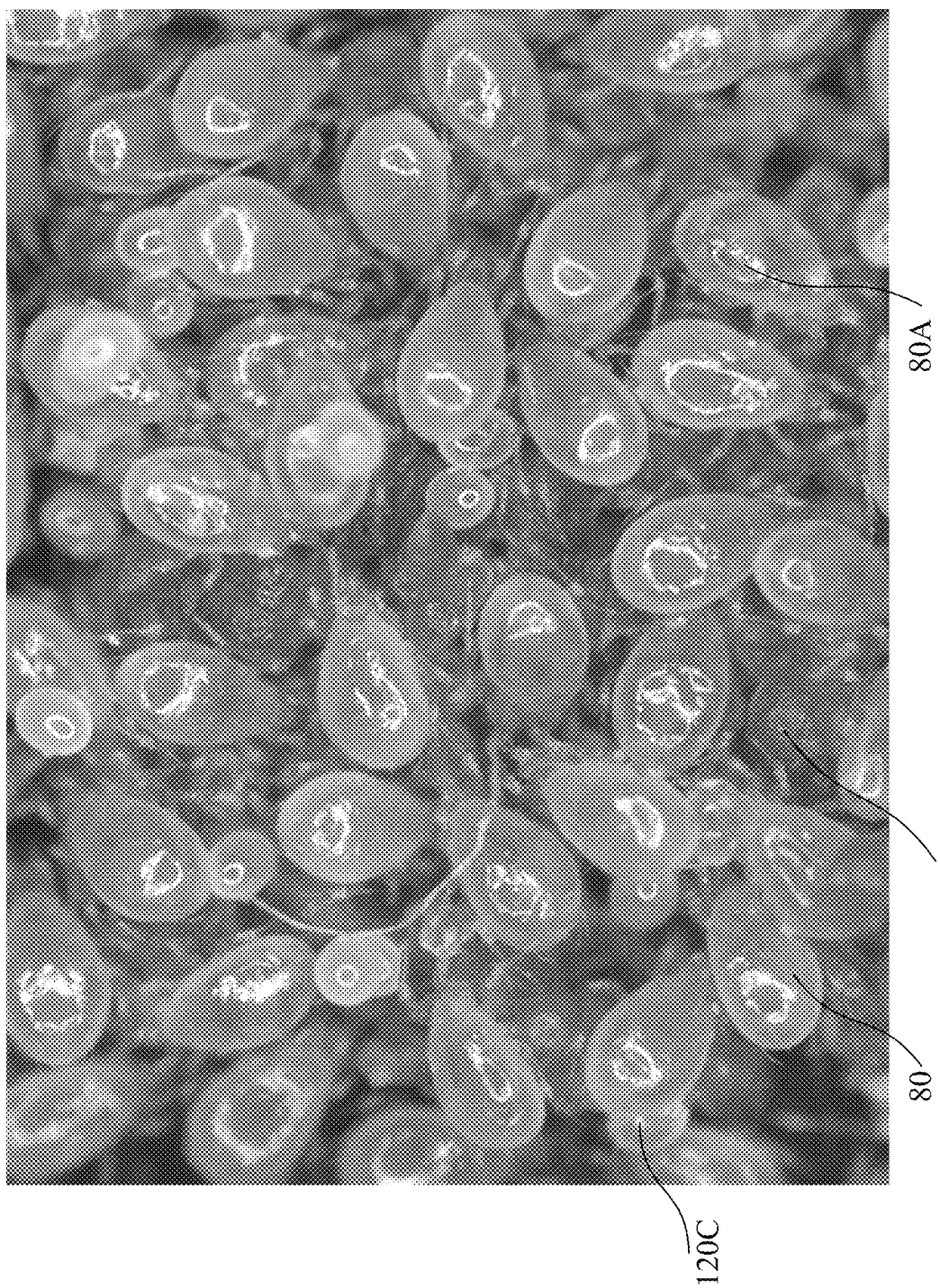
FIG. 6A is an example for natural enemies (predatory mites *Amblyseius swirskii*) feeding on feeding elements (prepared *Artemia* cysts), according to some embodiments of the invention.

FIG. 6A is an example for natural enemies 80 (predatory mites *Amblyseius swirskii*) feeding on feeding elements 120 (prepared *Artemia* cysts), according to some embodiments of the invention.

Figure 6B:
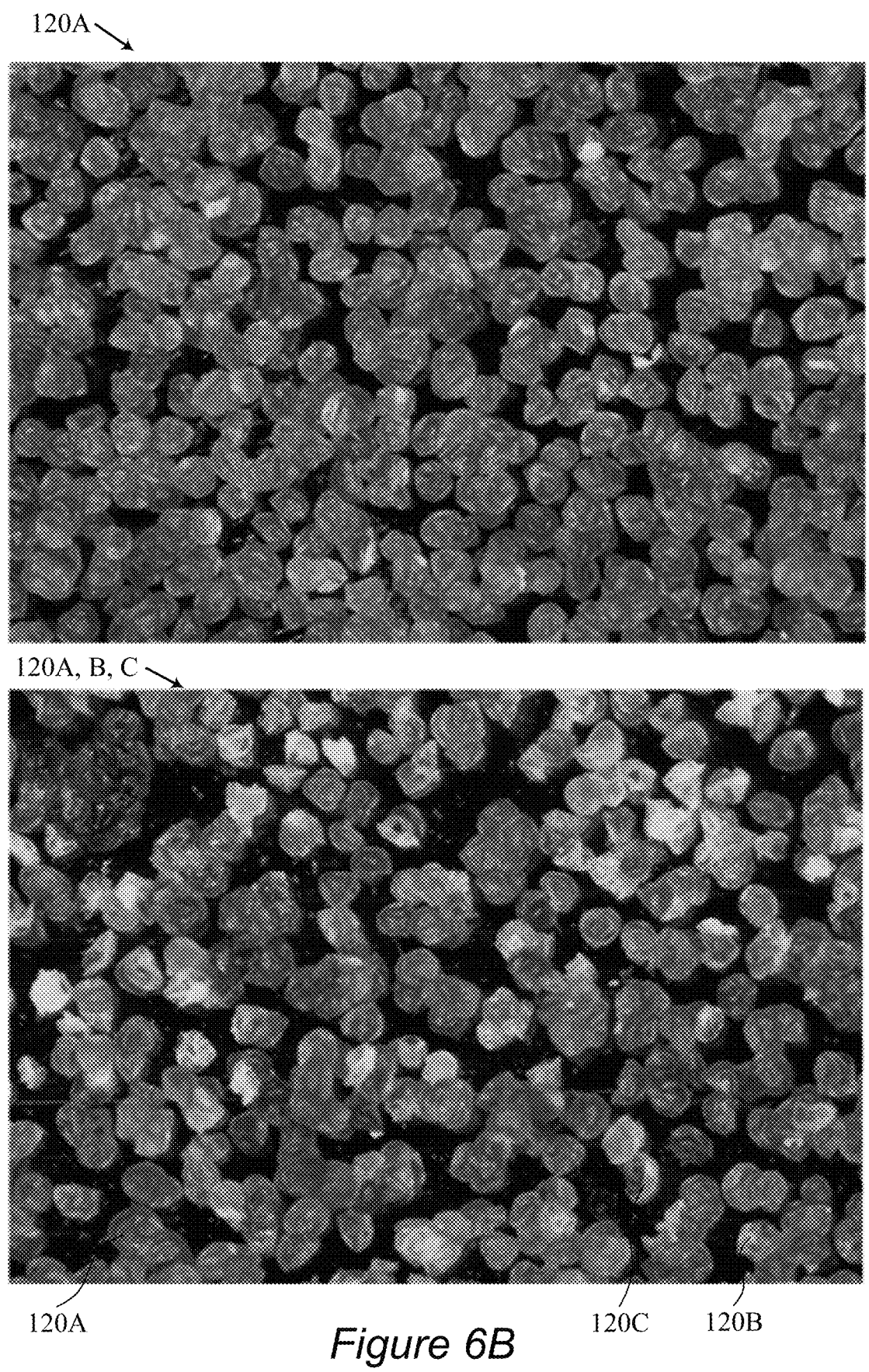
FIG. 6B is an example for the effects of feeding by the predators on *Artemia* cysts), according to some embodiments of the invention.

FIG. 6B is an example for the effects of feeding by the predators on *Artemia* cysts), according to some embodiments of the invention. The top image illustrates *Artemia* cysts 120A (full and viable cysts) which were not fed upon by predators, while the bottom image illustrates *Artemia* cysts 120A, 120B, 120C (full; partly fed-upon; and emptyfully fed-upon, respectively) after three days of feeding by predators.

It is noted that fresh and full cysts 120A are clearly distinguishable from empty cysts 120C and moreover, that mites that fed on cysts are distinguishable (80A) in their reddish color. FIG. 6A also exemplifies embodiments with internal feeding elements 120, e.g., within sachet-shaped mechanical supports 110 (see, e.g., FIG. 1D)—the cysts and mites may be within sachets 110B and emerge gradually out of sachet 110B onto the crop.

In certain embodiments, the color, or other visual aspects of feeding elements 120 may be used to indicate the extent to which feeding elements 120 are fed upon by the natural enemies, the extent to which the population of the natural enemies is developed, and/or the spatial range to feeding of the natural enemies.

FIG. 7A is a high-level schematic illustration of monitoring the population of natural enemies on plants 90 using platform 100, according to some embodiments of the invention. The inventors have noted that in certain cases, platform 100 may be further used as monitoring platform 100 for evaluating the extent of the population of natural enemies. Specifically, the color of the *Artemia* cysts is red when full and fresh (indicated schematically by black circles denoted by numeral 120A and corresponding arrow), yellow when partly fed upon and white when empty (indicated schematically by empty circles denoted by numeral 120C and corresponding arrow). The color of feeding elements 120 may be used to indicate the extent to which fresh feeding elements 120 are still available, indicate a need to provide additional feeding, e.g., applying additional platform(s) 100 to the crops, indicate the extent of spatial movements of the natural enemies and/or provide an estimation of the natural enemies' population size. Platform 100 may therefore be used both as feeding platform and as natural enemies monitoring platform. In certain embodiments, automation may be further implemented to enhance the monitoring, e.g., using image analysis algorithms to indicate tempo-spatial changes in visual aspects such as color of feeding elements 120 and derive therefrom population parameters and feeding elements 120 viability parameters. The inventors have found out that monitoring the state of feeding elements 120, e.g., monitoring the color of *Artemia* cysts as feeding elements 120 also provides data concerning the behavior of the natural enemies, e.g., *Orius* bugs tended to feed on platform segments which had direct contact to the surfaces of the plant leaves, while *Macrolophus* bugs typically also fed on platform segments which were suspended in the air without direct contact to the plant, corresponding to the typical mobility and behavior patterns of the corresponding insects. The *Amblyseius swirskii* mites typically fed partially on each egg, corresponding to the smaller size of the mites. *A. swirskii* mites that consumed cysts and became reddish, were encountered on upper plant parts while straps (as platforms 100) were applied one meter lower on the plant, indicating vertical mite movement on the plant to reach feeding elements 120. Mobility patterns and behaviors of the natural enemies may therefore be also monitored using platforms 100, providing possibility for dynamic management of the natural enemy population, before, during and after beginning of infestation of the plants by the pest species.

Figure 7B:
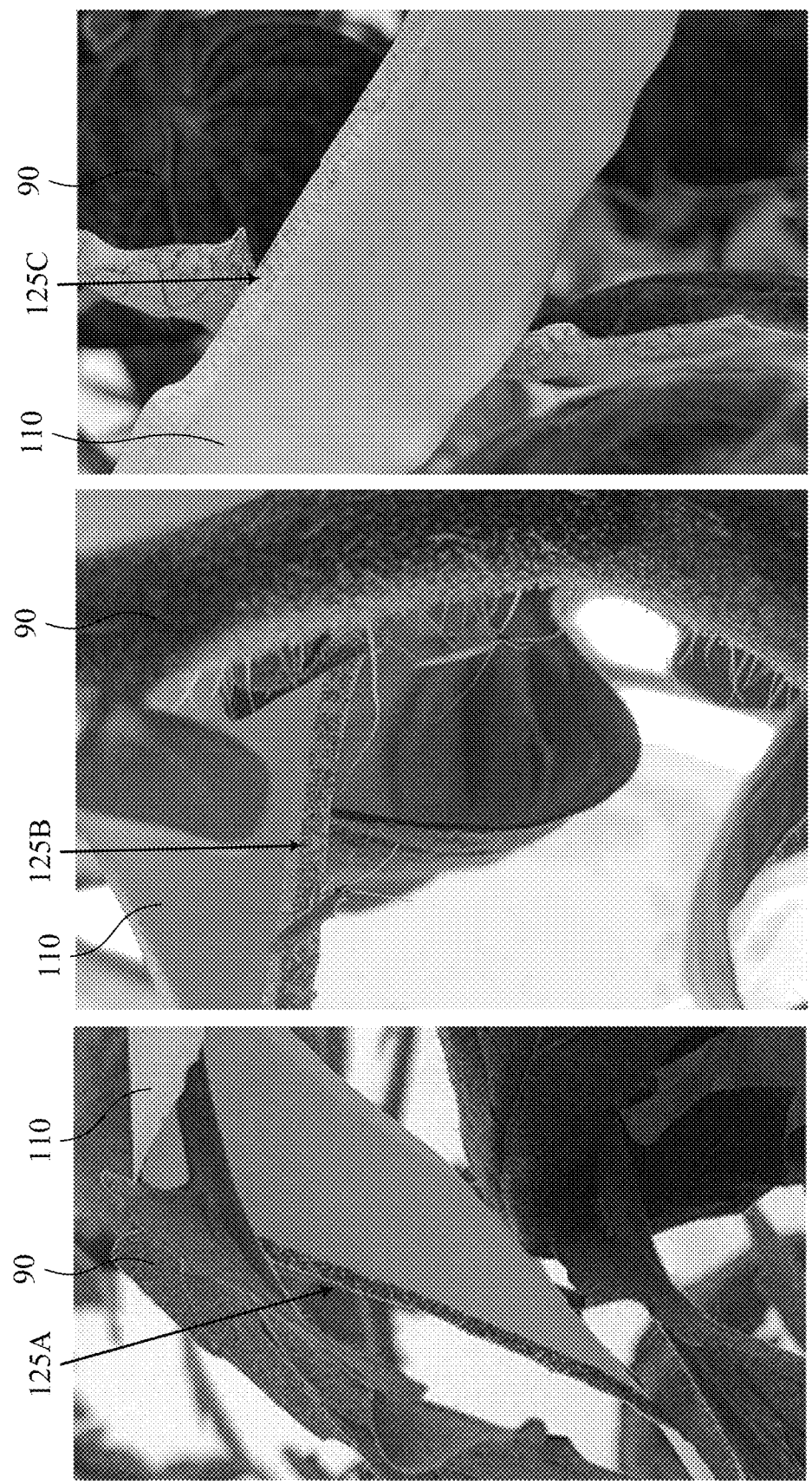
FIG. 7B illustrates three regions of mechanical supports of the platform, indicating different levels of feeding on the feeding elements by predators, according to some embodiments of the invention.

FIG. 7B illustrates three regions of mechanical supports 110 of platform 100, indicating different levels of feeding on feeding elements 120 by predators 80, according to some embodiments of the invention. Regions 125A, 125B and 125C indicate, e.g., by the color of the respective region, the level of feeding of the predators on feeding elements 120, specifically region 125A presents low or no feeding level (most or all cysts are red and fresh, in state 120A), region 125B presents a medium feeding level (some cysts are red and fresh, in state 120A, some cysts are white and empty, in state 120C and some cysts are in intermediate, partly fedupon state 120B), and region 125C presents high feeding level (most or all cysts are white and empty, in state 120C). FIG. 7B clearly shows the efficiency of the monitoring method disclosed above.

The experimental evidence indicates that disclosed platforms 100 and methods 200 provide a generic approach for feeding generalist predators in biological control, being neither predator nor crop specific, as it was successfully applied to key predatory taxa used in biological control (from phytoseiid predatory mites to predatory bugs, both mirids and anthocorids) and to various crops and additional plants (tomato, sweet pepper and cucumber, initial data also for strawberry and *cannabis*, indicating additional plants are good candidates).

Advantageously, disclosed platforms and methods enhance the "predator in first" or "standing army" approach (aimed at establishing predatory natural enemies before pest prey arrives to or established on the plants) in that their application is simpler, more accurate and more efficient than prior art methods. For example, in the prior art, food material for natural enemies is spread either manually by sprinkling the food material from a dispenser on the crop or mechanically using an air blower to blow the food material on the crop. Disclosed platforms 100 and methods 200 overcome the shortcomings of these methods. In both prior art cases, the food is applied directly on the foliage, where overhead irrigation or sprays can easily wash it off. Moreover, the leaf surface is a humid environment and is designed to absorb UV, which results in a high rate of decrease in the quality of the food applied on the plant foliage or near the plant foliage. For these reasons, it is necessary in the prior art to apply the food frequently, typically once every 3-14 days, making prior art methods expensive and labor intensive. Blower application of food inevitably results in wastage of food that falls on the growing substrate or soil rather than on the leaves, particularly before the crop foliage is fully developed. Moreover, proper blower application requires training to reduce waste and achieve even distribution of the food on the crop. As disclosed above, disclosed platforms 100 and methods 200 disperse food elements evenly, not directly on foliage but in close proximity thereto, partly protect the food elements thereby increasing durability after application, use food elements economically, and are simple to implement.

Certain embodiments comprise the preparation of the *Artemia* cysts to remain fresh (effective as feed) for several weeks, e.g., at least three, four, seven or more weeks, depending on environmental conditions (see, e.g., FIGS. 11A and 11B below). The inventors have found out ways to modify the application and production methods of *Artemia* cysts to be usable and useful in platforms 100 and methods 200 disclosed herein. Moreover, disclosed production processes and methods may be further used to enable using high quality *Artemia* cysts in mass rearing of predatory arthropods in various circumstances, not only for disclosed platforms 100 and methods 200 and not only for crops. While cysts of the brine shrimp *Artemia* spp. are known as feed for fish in the aquaculture, and while attempts have been made to use *Artemia* cysts as feed for insects, the industrial production of high-quality dry decapsulated cysts as feed for insects was not successful until now. One of the barriers to using *Artemia* cysts as feed for insects is that the hard shells of the cysts prevent effective feeding by predatory arthropods and must be removed (see, e.g., De Clercq et al. 2005, Nutritional value of brine shrimp cysts as a factitious food for *Orius laevigatus* (Heteroptera: Anthocoridae), Biocontrol Science and Technology, 15:5, 467-479; Vandekerkhove et al. 2009, *Artemia* cysts as an alternative food for the predatory bug *Macrolophus pygmaeus*, J. Appl. Entomol 133 (2): 133-142; Nguyen et al. 2014, Artificial and factitious foods support the development and reproduction of the predatory mite *Amblyseius swirskii*, Exp Appl Acarol 62 (2):181-194; and Vangansbeke et al. 2014, Performance of the predatory mite *Amblydromalus limonicus* on factitious foods. BioControl 59 (1):67-77).

Moreover, while there are available protocols in the literature for small scale cyst decapsulation as feed for fish (e.g., Bruggeman et al. 1980, Improvements in the decapsulation technique of *Artemia* cysts, in: Persoone, G. et al. (Ed.) The brine shrimp *Artemia*: Proceedings of the International Symposium on the brine shrimp *Artemia salina*, Corpus Christi, Tex., USA, Aug. 20-23, 1979: 3. Ecology, culturing, use in aquaculture. pp. 261-269; and Lavens and Sorgeloos 1996, Manual on the production and use of live food for aquaculture. FAO Fisheries. Technical Paper 361, Rome), the end-product of these protocols is a wet feed for direct use or for wet storage in brine, which is not applicable as dry feed for insects in platforms 100 and methods 200 disclosed herein. It is noted that while there are dry decapsulated cyst products on the market (appropriate only for the mirid *Macrolophus pygmeus*), these products are of poor quality as feed for insects, not useful for other predatory insects and do not match the quality reported on in the literature. As the inventors found out that no appropriate decapsulated *Artemia* cysts are available on the market and that no industrially viable production method of decapsulated *Artemia* cysts as feed for most species of predatory arthropods is available, the inventors have developed the following disclosed process to yield the required decapsulated *Artemia* cysts for use in platforms 100 and methods 200 as well as for other uses as insect feed, e.g., in mass rearing of predatory arthropods and on crops, to increase predator numbers and improve biocontrol.

*Artemia* cysts prepared according to the following procedure were demonstrated to be superior to prior art *Artemia* cysts as dry feed and can be used to feed a wide range of predators as shown for key groups of generalist predators applied in biocontrol: Anthocoridiae (predatory bugs) and Phytoseiidae (predatory mites).

In certain, non-limiting embodiments, dry, non-decapsulated cysts were hydrated in water and then decapsulation was started using cooled sodium-hypochlorite and/or calcium hypochlorite solution together with a sodium-hydroxide and/or calcium oxide and/or sodium carbonate solution. Following decapsulation, the decapsulated cysts were removed from the fluid (e.g., by sieving, filtering, centrifugation or other methods) and transferred to a sodium-thiosulfate bath (or washed in water and/or placed in a water bath), to neutralize the active chlorine. Following additional purification, e.g., additional washing and separation from remaining debris, the decapsulated cysts were transferred to a bath with preservatives, e.g., potassium sorbate, methylparaben or a combination of both. It is noted that high quality decapsulated *Artemia* cysts were also produced without using preservatives, and that applying preservatives to the decapsulated *Artemia* cysts is optional. Additional preservatives (e.g., general preservatives, antifungal agents, antibacterial agents and/or agents against protozoa) are listed below, and may be used on decapsulated *Artemia* cysts and/or on added carrier material. Following additional separation (e.g., by sieving, filtering, centrifuging, etc. and optional washing), the decapsulated cysts were dried, e.g., to a water content<10% within six hours in hot air dryers and under continuous mixing to avoid clump forming. Air temperature in the dryers was limited to 60° C. to avoid damage to the decapsulated cysts. In certain embodiments, air temperature in the dryers may be set to temperatures within the range of 35° C.-80° C. The decapsulated dry cysts were sieved to avoid clumps larger than a specified size, e.g., any of 100 µm, 200 µm 300 µm, 400 µm, 500 µm or intermediate values. in the end product. In certain embodiments, clumps may be set to be up to 1 mm in size. After this process, the dry cysts may be mixed with sawdust or another carrier material as disclosed herein, or packed without a carrier material. The prepared cysts were then packed in sealed containers to avoid rehydration and stored under dark and cool (6° C.) conditions, to maximize shelf-life.

Surprisingly, the inventors have found out that the quality of the decapsulated cysts as feed for predatory arthropods was positively correlated with the hatching percentage (H %) of the original, non-decapsulated *Artemia* cysts, which represents the percentage of cysts which contain embryos that hatch to nauplii under ideal conditions. Moreover, different predatory arthropod groups proved to have different H % thresholds for successful development and reproduction on of the respective predatory arthropods on the decapsulated *Artemia* cysts.

Figure 9A:
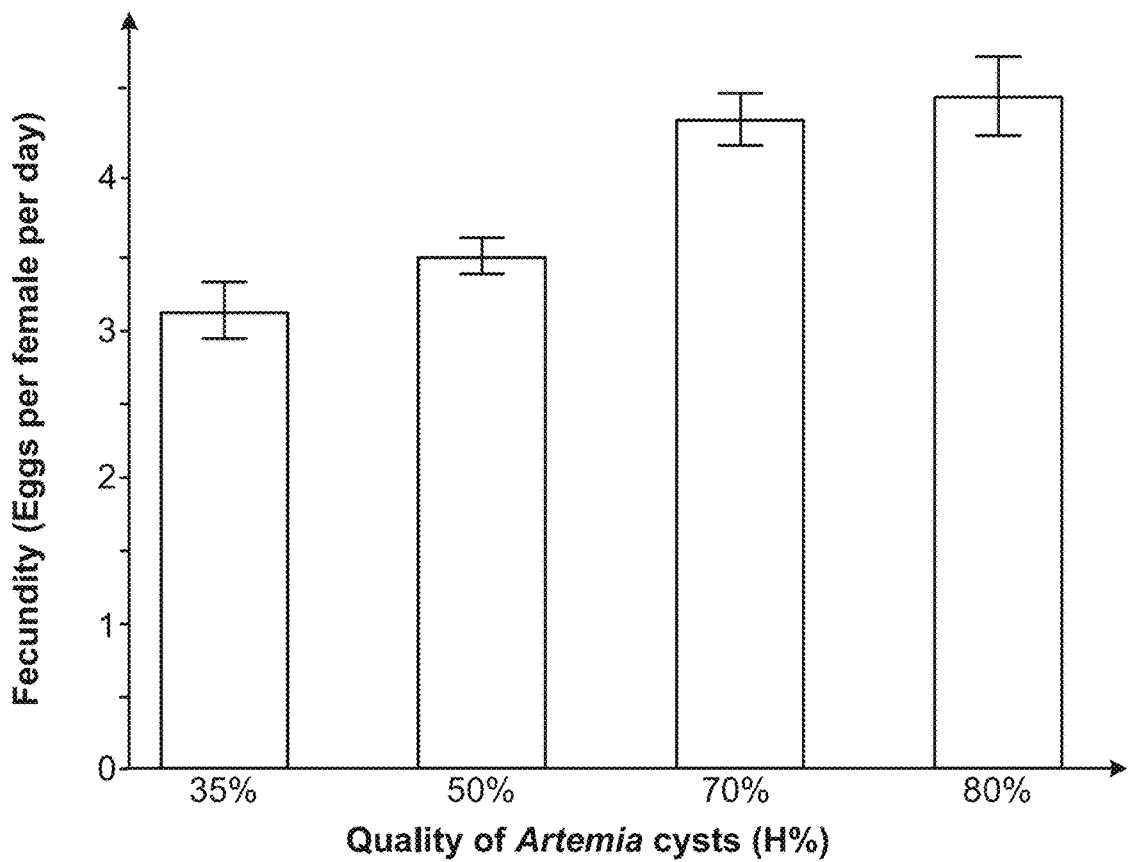
FIG. 9A presents experimental results of the fecundity of the minute pirate bug *Orius laevigatus* feeding on decapsulated *Artemia* cysts with various hatching percentages, according to some embodiments of the invention.

For example, trials have shown that *Orius laevigatus* (Anthocoridae) requires cysts with H % higher than 70% to reproduce optimally, but can also reproduce on cysts with H % as low as 35% (Trial 1; FIG. 9A). In contrast, the survival and development of *Amblyseius swirskii* (Phytoseiidae) populations was not successful on cysts with H % between 35%-70% (Trial 2) but was successful on decapsulated cysts produced from H %=80% and above. These trials demonstrate that in order to produce a feed product for phytoseiids, anthocorids, or other predatory arthropods, it is necessary to use *Artemia* cysts with corresponding H %, e.g., H % higher than 80%. Moreover, in a direct comparison between the *Artemia* cysts that were decapsulated as disclosed above from cysts having original H %=80% and prior art available decapsulated *Artemia* cyst products, it was shown that the former are superior as feed for all tested predator species (*M. pygmeus*, Trial 3; *O. laevigatus*, Trial 4; *A. swirskii*, Trial 5).

Moreover, the inventors have found out that using cooled decapsulation compounds was beneficial and advantageous in preventing damage to the cysts that reduces their quality as feed for predatory arthropods in the disclosed applications. The inventors note that commercial scale decapsulation involves heating the cysts due to the exothermic nature of the process, which may be a cause for the resulting inferior product. While Bruggeman et al. 1980 suggest using a cooling system, the inventors have found out that using pre-cooled decapsulation agents achieved the required maintenance of the cysts' viability. For example, the hypochlorite solution may be cooled to −18° C., so that in combination with the other ingredients, the temperature of the decapsulation solution is reduced to under 5° C. at the start of the decapsulation process. The inventors have moreover taken care to prevent overheating of the cysts during the processes, e.g., keeping them below 20° C. to avoid heat damage.

Finally, drying the cysts is a crucial step, as cyst decapsulation is a wet process and after decapsulation, the water content of the cysts should be reduced as soon as possible below the critical level of 10% in order to stop the metabolic activity and consequently ensure a long shelf life and optimal quality of the decapsulated cysts. Certain embodiments comprise treating the cysts in a centrifuge immediately after decapsulation to reduce the water content in the wet decapsulated cyst mass by approximately 50%, to allow for a drying period shorter than six hours that prevents quality loss during drying. Detailed experiments were carried out to optimize the centrifugation parameters with respect to the drying parameters, to maximize the viability and quality of the cysts (Trial 6).

The formulation of preservatives was also optimized to maximize the post-application durability of the *Artemia* cysts, which is required and beneficial in platforms 100 and methods 200, in particular with respect to reduction of mold development on the cysts post application (Trial 7). The formulation was tested and proved safe for consumption by predatory arthropods (*M. pygmeus*, Trial 8; *O. laevigatus*, Trial 9; *A. swirskii*, Trial 10). As a result, fewer feed applications are required as disclosed above and higher efficiency in maintaining the populations of the predatory arthropods is reached.

In various embodiments, various general preservatives, antifungal agents, anti-bacterial agents and/or agents against protozoa may be used to extend the lifetime of the decapsulated *Artemia* cysts and/or platforms 100. Non-limiting examples may include any of: (i) general preservatives such as formalin, o-Phenylphenol, Bradosol® (domiphen bromide), ethanol, etc.; (ii) antifungal agents such as benzoic acid (also sodium benzoate, potassium, benzoate), methyl paraben, propyl paraben, sorbic acid (also potassium sorbate and sodium sorbate), propionic acid, Benlate® (Benomyl), sodium propionate, citral, geranial, neral, natamycin (pimaricin), amphotericin B, nystatin, etc.; (iii) anti-bacterial agents such as nisin, streptomycin sulfate, Aureomycin® (chlorotetracycline), Oxytetracycline (Oxacycline, Terraject®, Terramycin®, kanamycin sulfate, Aerosporin® (Polymyxin), Albamycin® (novobiocin), Bacitracin®, Chloromycetin® (chloramphenicol), Erythrocin® (erythromycin), Gantrisin® (sulfisoxazole), Kantrex® (kanamycin), mycifradin sulfate (neomycin), penicillin G potassium, streptomycin sulfate, Tetracyn® (tetracycline), Vanocin® (vanomycin) etc.; agents against protozoa such as Fumadil B® (also Fumidil, Fumagillin), and so forth.

Figure 8A:
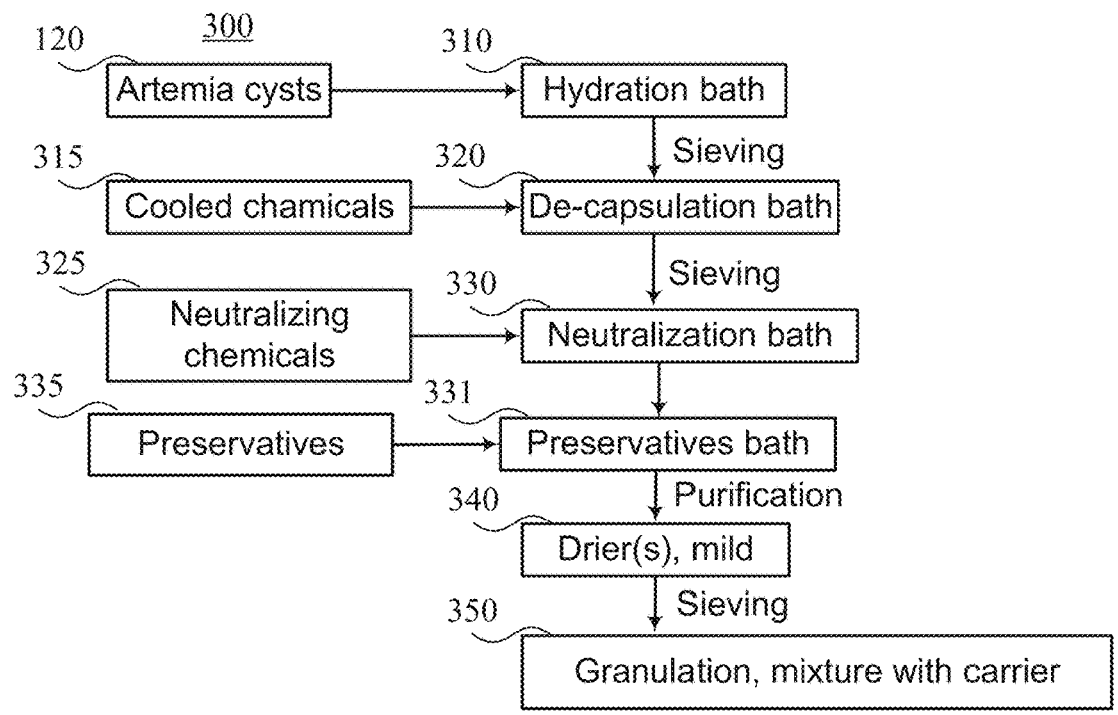
FIGS. 8A and 8B are high-level schematic illustrations of systems and methods, respectively, of preparing decapsulated *Artemia* cysts as feed for predatory arthropods which is effective as feed for at least three weeks post application, according to some embodiments of the invention.
Figure 8B:
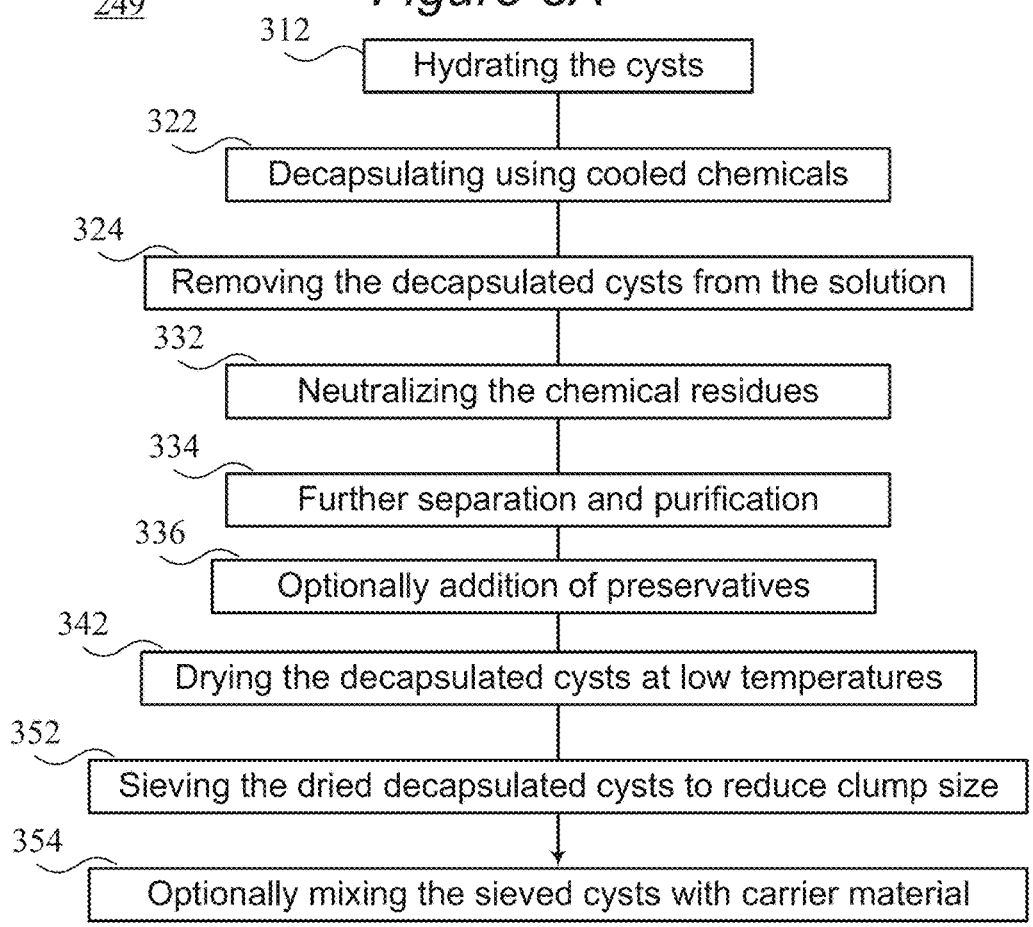

FIGS. 8A and 8B are high-level schematic illustrations of systems 300 and methods 249, respectively of preparing decapsulated *Artemia* cysts as feed for predatory arthropods which is effective as feed for at least three weeks post application, according to some embodiments of the invention. It is noted that the usability of any feed also depends on the relative humidity (RH) in the environment in which it is applied, with lower RH extending the usability period. For example, decapsulated *Artemia* cysts may be effective as feed for at least seven weeks under average relative humidity which is up to 70%, or even longer under average RH of 60%, but only effective as feed for at least four weeks under average relative humidity which is up to 80%, and effective as feed for fewer, e.g., two or three weeks post application under average RH of 90% (see, e.g., FIGS. 11A and 11B below)—for decapsulated *Artemia* cysts applied on platform 100. Also in case of foliar application, decapsulated *Artemia* cysts prepared as disclosed herein may be effective as feed longer than prior art decapsulated *Artemia* cysts and at least as long as other feed sources such as pollen as *Ephestia* eggs, as shown herein.

Methods 249, which may be part of methods 200 disclosed above or independent methods 249, comprise hydrating *Artemia* cysts (stage 312), e.g., in a hydration bath 310, decapsulating the hydrated *Artemia* cysts using cooled chemicals 315 (stage 322), e.g., in a de-capsulation bath 320, followed by separation and neutralization of the decapsulated cysts (stages 324, 332, 334), e.g., using neutralizing chemicals 325 in a neutralization bath 330, optionally adding preservatives 335 to the decapsulated cysts to further extend their viability period (stage 336), e.g., in a preservatives bath 331, drying the decapsulated cysts mildly (stage 342), maintaining their quality as feed according to specified criteria, e.g., in drier(s) 340, and preparing the dried decapsulated cysts as the feeding elements, e.g., by sieving or granulating the dried decapsulated cysts to reduce clump size (stage 352) and optionally mixing the sieved cysts with carrier material (stage 354)—to yield a granulated mixture of carriers 350 that may be used in platforms 100 and methods 200. For example, decapsulated *Artemia* cysts as feeding elements 120 may have a hatching percentage (H %) larger than 30%—which was found to be sufficient for some predatory arthropods, e.g., *Orius* and *Macrolophus* bugs (see e.g., FIG. 9A for *Orius*), larger than 50%, larger than 80%—which was found to be sufficient for some predatory arthropods, e.g., predatory mites, and/or larger than 90% and may be prepared as feed for predatory arthropods which is effective as feed for at least three weeks post application, at least six weeks and/or at least three months. It is noted that more mobile predatory arthropods (e.g., bugs) may require a lower level of hatching percentage (H %) of the treated *Artemia* cysts than less mobile predatory arthropods (e.g., mites).

FIG. 9A presents experimental results of the fecundity of the minute pirate bug *Orius laevigatus* feeding on decapsulated *Artemia* cysts with various hatching percentages (Trial 1), according to some embodiments of the invention. 150-200 young adult bugs (ca. 80%) and mature nymphs (ca. 20%) were fed for four days on decapsulated *Artemia* cysts having different hatching percentages (H %) spread on feeding cards in cells that also included paper towels and two bean pods each, and were ventilated and kept at 70% relative humidity (RH) and 22° C., and consecutively groups of ten females each were transferred into incubation chambers, each with a feeding card, bean pod and paper towel, that were kept at 70% relative humidity and 24° C. for additional four days. The fecundity was measured as the number of eggs per female and day, and is shown in FIG. 9A to steadily rise as the viability of the decapsulated *Artemia* cysts (H %) is higher.

Additional experiments were carried out (as Trial 2) with the predatory mite *Amblyseius swirskii*, which illustrated increasing development and survival rates when fed with decapsulated *Artemia* cysts having increasing hatching percentages. The trials were carried out in a flat plastic arena (8×15 cm$^2$) having edges covered with wet tissue paper, to provide water and prevent escape of the mites. Eggs of the predatory mite *A. swirskii* were placed on the arena along with a piece of tape with decapsulated artemia cysts, as a food source. Treatment differed in the H % grade of the artemia cysts used to produce the decapsulated artemia cysts: 30%, 50%, 70% and 80%. Each treatment was tested in two repetitions (arenas), each containing 150 individuals. After 24 hours the remaining *A. swirskii* eggs were removed, so that only mobile stages with a maximal age of 24 hours were left on the arena. The arenas were incubated in a climate room at 25° C., 80% RH and 16:8 L:D light regime. The development of *A. swirskii* was recorded on the arenas for a period of two weeks, after which, *A. swirskii* females start egg laying, when kept with suitable diet. Two weeks after the start of the trials, the arenas were evaluated to check if there were sufficient females to conduct a fecundity trial. Survival was very low on the arenas fed with 30%, 50% and 70% H % grade artemia cysts. Two weeks after trial start, the few surviving individuals did not start oviposition, and appeared pale and thin. A fecundity trial was therefore not conducted. On the arena fed with 80% H % grade *Artemia* cysts, survival was high, fully developed adult females were abundant and oviposition started. As proper development and fecundity were only identified on *Artemia* cysts with 80% H %, further trials were conducted only with *Artemia* from this quality. In further trials, the dietary quality of 80% H % decapsulated artemia cysts was compared to alternative feeds that are applied as diet for *A. swirskii*.

Figure 9B:
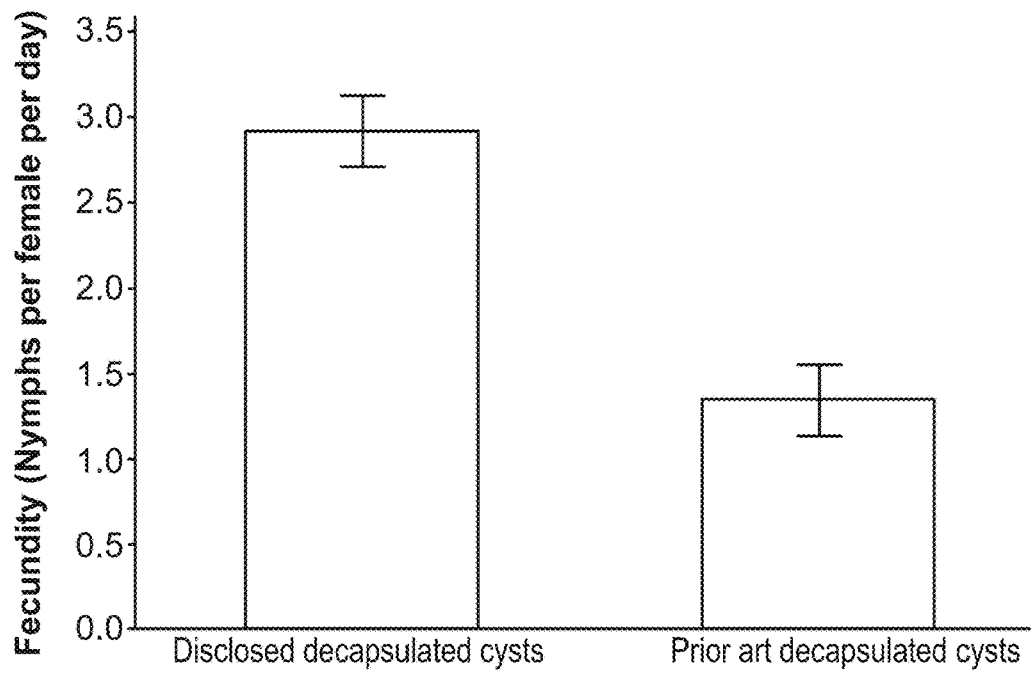
FIG. 9B presents experimental comparison of the fecundity of the mirid bug *Macrolophus pygmeus* feeding on prior art decapsulated *Artemia* cysts with the decapsulated *Artemia* cysts prepared as disclosed herein, according to some embodiments of the invention.

FIG. 9B presents experimental comparison (Trial 3) of the fecundity of the mirid bug *Macrolophus pygmeus* feeding on prior art decapsulated *Artemia* cysts (available on the market) with the decapsulated *Artemia* cysts (with 80% H %) prepared as disclosed herein, according to some embodiments of the invention. Ca. 150 mature nymphs and young adult bugs were fed for two days on the respective decapsulated *Artemia* cysts spread on feeding cards in cells that also included paper towels and bean pods and were ventilated. Adults were then collected and were kept in similar cells for seven days, during which they were fed twice with the respective decapsulated *Artemia* cysts. Then, the adult bugs were allowed to lay eggs on tomato seedlings, enclosed with feeding cards having the respective decapsulated *Artemia* cysts for a week. After the bugs were removed, the cells were sealed and supplied with additional feeding cards, and the number of resulting *M. pygmeus* bugs was counted two weeks after sealing the cells, to compare the fecundity of *M. pygmeus* under the two feeding conditions. As shown in FIG. 9B, disclosed decapsulated *Artemia* cysts yielded highly superior results with respect to prior art decapsulated *Artemia* cysts.

Figure 9C:
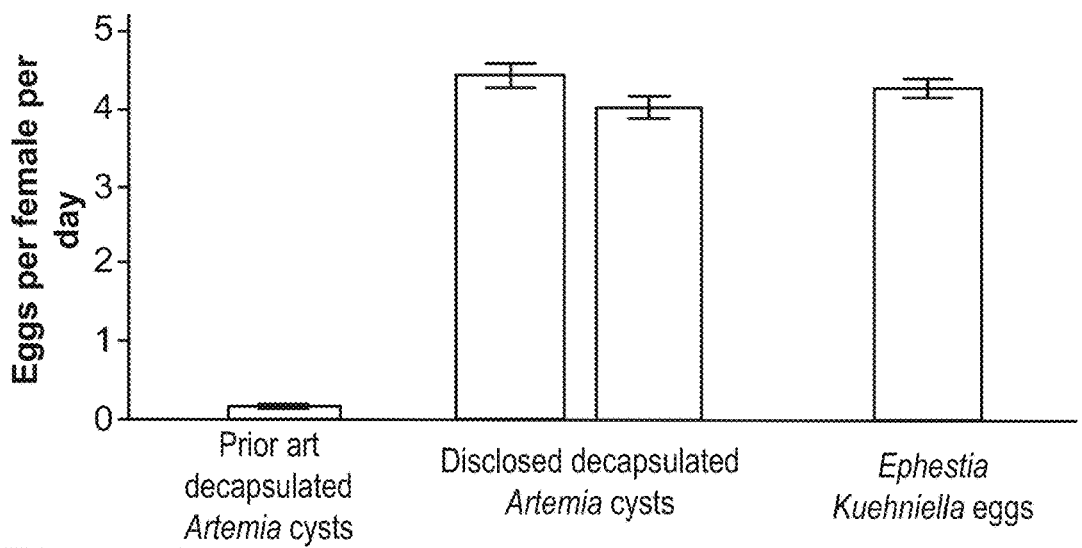
FIG. 9C presents an experimental of the fecundity of *Orius laevigatus* on prior art decapsulated *Artemia* cysts (available on the market) and other prior art feed with the decapsulated *Artemia* cysts (with 80% H %) prepared as disclosed herein, according to some embodiments of the invention.

FIG. 9C presents an experimental comparison (as Trial 4) of the fecundity of *Orius laevigatus* on prior art decapsulated *Artemia* cysts (available on the market) and other prior art feed with the decapsulated *Artemia* cysts (with 80% H %, results from two experiments) prepared as disclosed herein, according to some embodiments of the invention. *Orius* bugs are often fed with *Ephestia kuehniella* eggs as standard high-quality feed in mass rearing. The application of this feed to boost *Orius* populations in greenhouses is very limited, because of its high price and short post-application durability of several days. Feeding *Orius* with decapsulated artemia cysts was not possible so far, because the quality of standard decapsulated cyst products was too low, as explained above. However, disclosed decapsulation methods 249 and systems 300 were shown to have a similar feeding quality as the *Ephestia* eggs, and a much higher quality than the standard decapsulated cyst products, as illustrated in FIG. 9C.

Figure 9D:
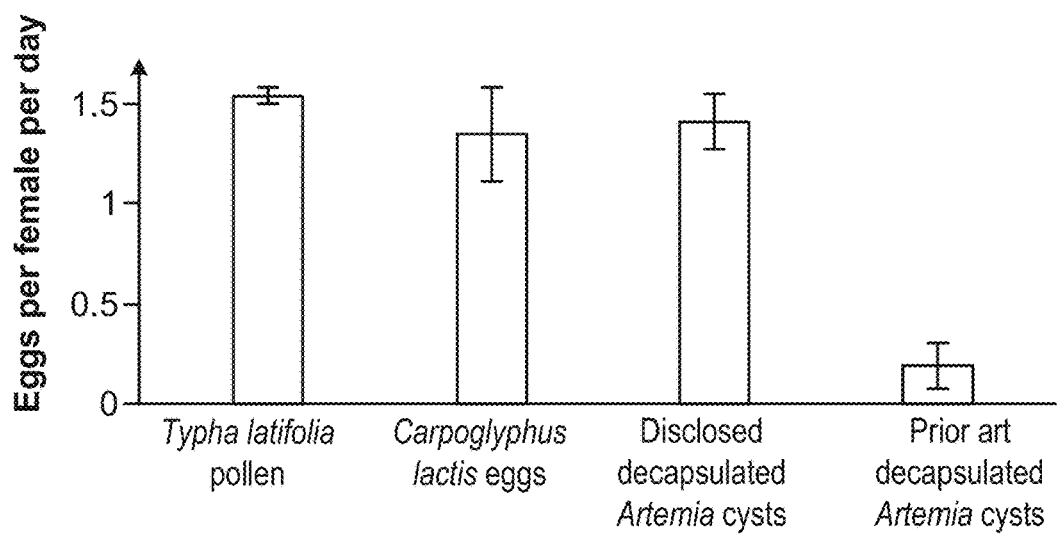
FIG. 9D presents an experimental comparison of the fecundity of the predatory mite *Amblyseius swirskii* feeding on prior art decapsulated *Artemia* cysts and other prior art feeds, with the decapsulated *Artemia* cysts prepared as disclosed herein, according to some embodiments of the invention.

FIG. 9D presents an experimental comparison (as Trial 5) of the fecundity of the predatory mite *Amblyseius swirskii* feeding on prior art decapsulated *Artemia* cysts (available on the market) and other prior art feeds, with the decapsulated *Artemia* cysts (with 80% H %) prepared as disclosed herein, according to some embodiments of the invention. Rearing methods were similar to Trial 2, but in this trial adult females were collected from the arena two weeks after trial's start. Females were isolated in cells, each containing two females, a feeding card with the tested diet and moist cotton thread as water source, additional feeds were pollen of *Typha latifolia* and eggs of *Carpoglyphus lactis*, which are used in the art as feed for predatory arthropods. As shown in FIG. 9D, disclosed decapsulated *Artemia* cysts yielded highly superior results with respect to prior art decapsulated *Artemia* cysts, and similar results to alternative feed sources.

Figure 9E:
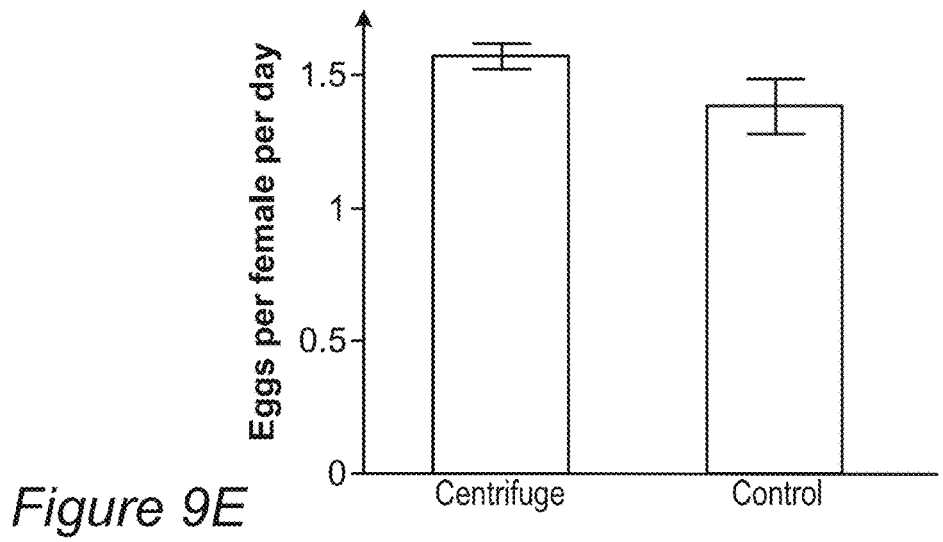
FIG. 9E presents experimental results concerning the effect of centrifuge treatment before drying step, on the quality of the dry decapsulated *Artemia* cysts as feed for *A. swirskii*, according to some embodiments of the invention.

FIG. 9E presents experimental results (as Trial 5) concerning the effect of centrifuge treatment before drying step 342, on the quality of the dry decapsulated *Artemia* cysts as feed for *A. swirskii*, according to some embodiments of the invention. The results indicate that centrifugation is advantageous for more efficient drying that maintains the viability of the cysts. Moreover, the results show that centrifuge treatment improved the quality of the end product as feed for *A. swirskii*.

Figure 10A:
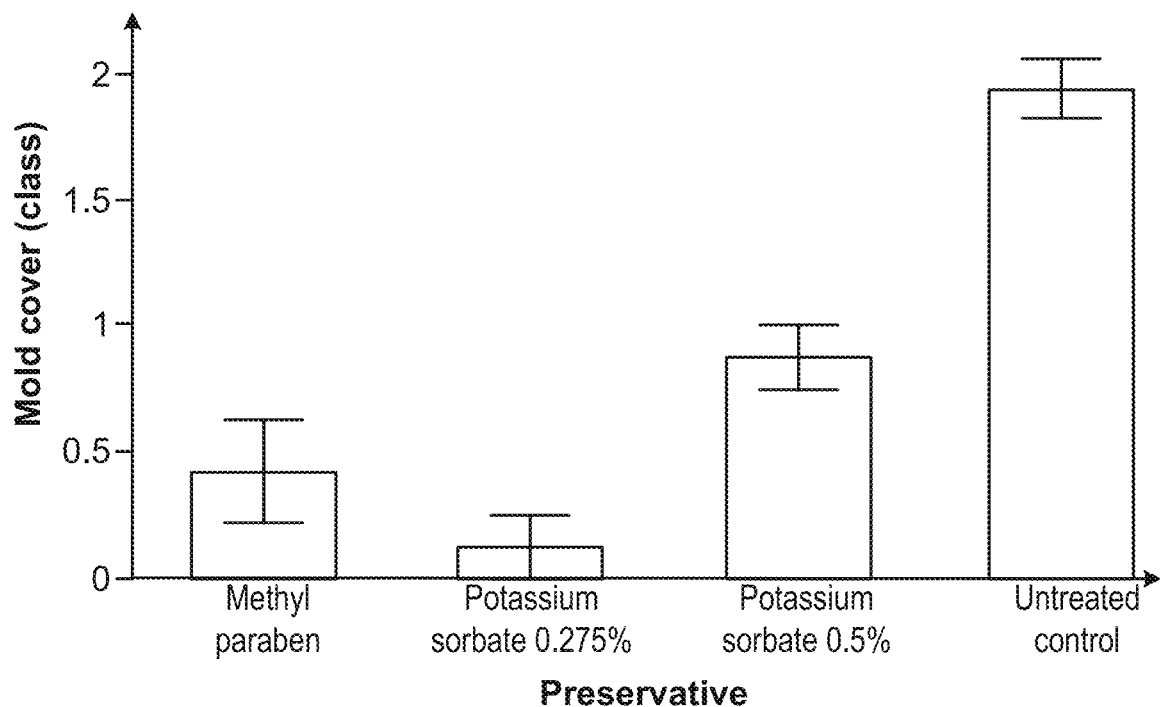
FIGS. 10A-10D present experimental results concerning the effect of adding preservatives to impede development of molds on the decapsulated *Artemia* cysts upon their application as feed for predatory arthropods, according to some embodiments of the invention.
Figure 10B:
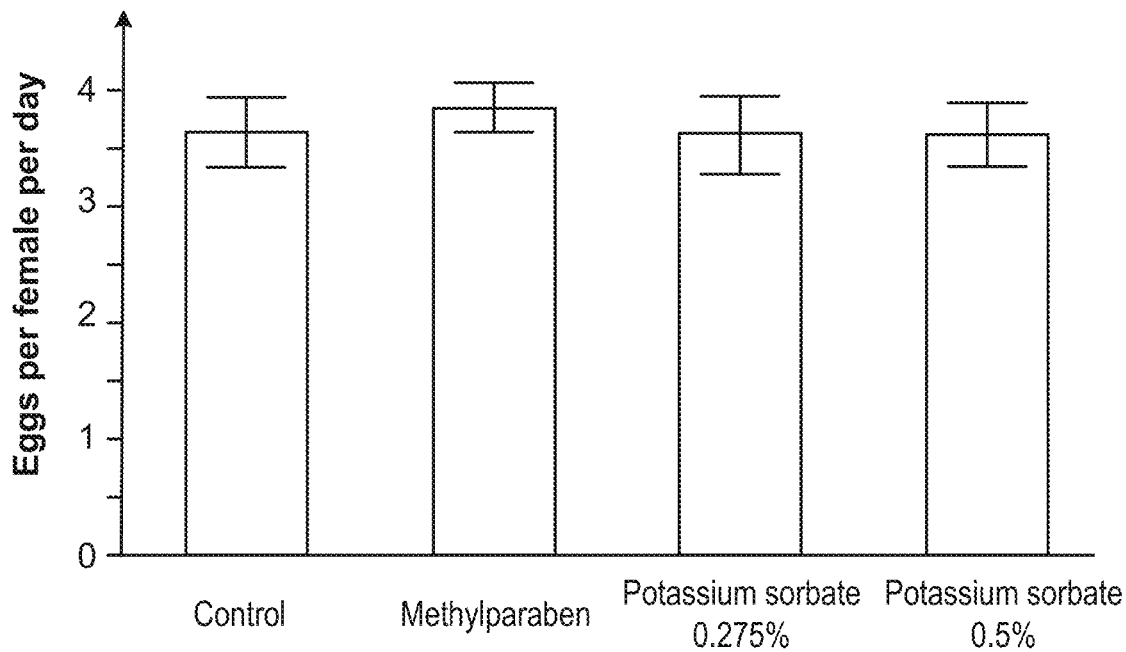
Figure 10C:
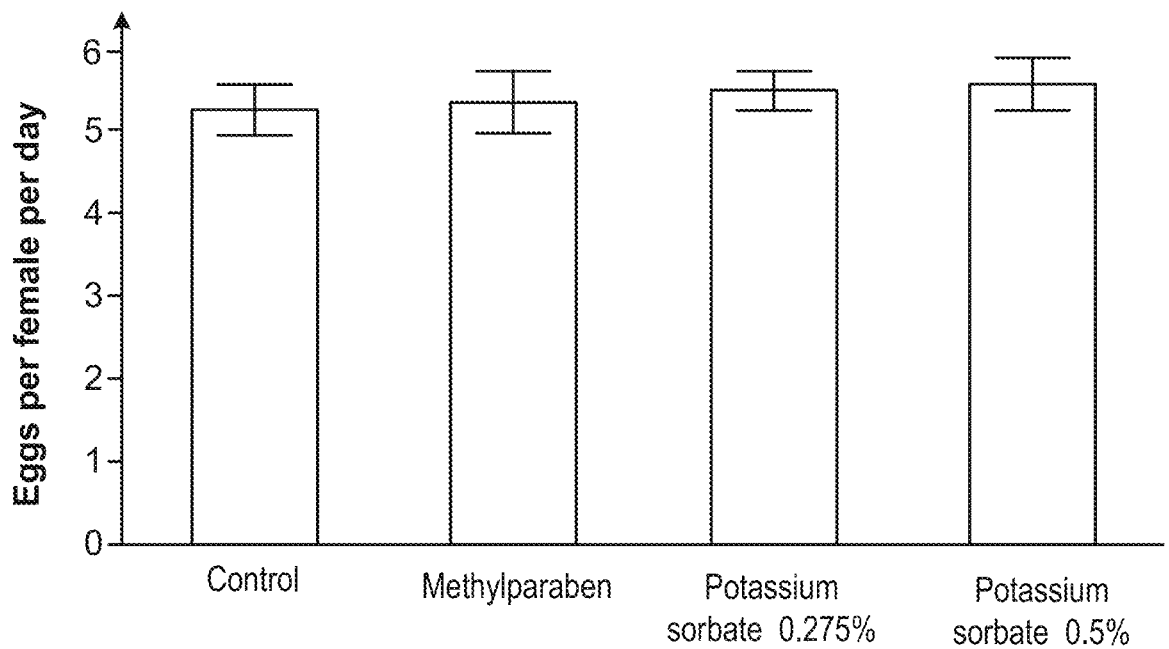
Figure 10D:
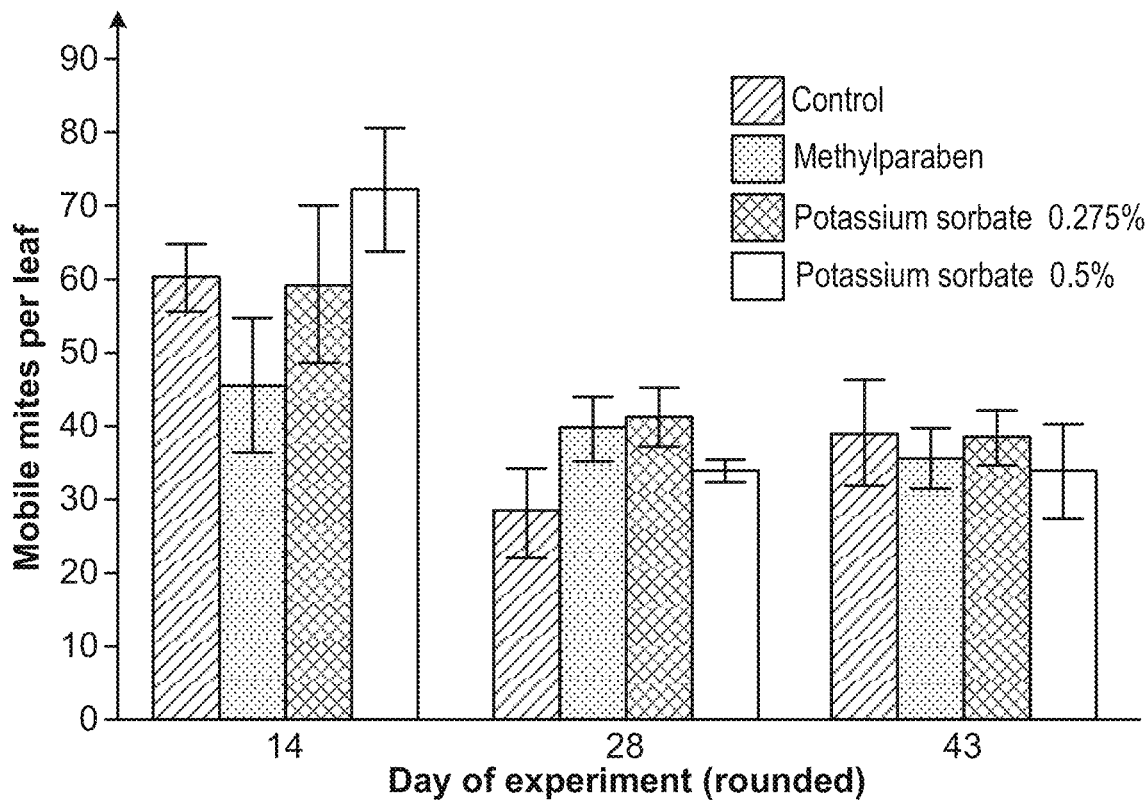

FIGS. 10A-10D present experimental results (as Trials 7-10, respectively) concerning the effect of adding preservatives (stage 336) to impede development of molds on the decapsulated *Artemia* cysts upon their application as feed for predatory arthropods, according to some embodiments of the invention. FIG. 10A (Trial 7) presents results comparing different preservatives (after seven days of incubation at 25° C. and 92% RH), illustrating the efficiency of all preservatives, and particularly of potassium in preventing molding of decapsulated *Artemia* cysts. FIG. 10B (Trial 8) presents results comparing different preservatives with respect to the fecundity of *M. pygmeus*, with experimental setting similar to Trial 3, showing that the preservatives did not significantly reduce the fecundity of the predatory bugs. FIG. 10C (Trial 9) presents results comparing different preservatives with respect to the fecundity of *O. laevigatus*, with experimental setting similar to Trial 1, showing that the preservatives did not significantly reduce the fecundity of the predatory bugs. FIG. 10D (Trial 10) presents results comparing different preservatives with respect to the fecundity of *A. swirskii*, using cucumber seedlings in a semi-field trial. An experimental unit consisted of a fine gauze cage containing five cucumber plants. Per plant, 25 adult female predators were released and decapsulated *Artemia* cysts were applied on three leaves, once in two weeks. Treatments differed in the preservative applied during the production process. The trial shows that the preservatives did not significantly reduce the population development of the predatory mites, as compared to the untreated control cysts.

Concerning the concentrations of the preservatives, it is noted that following extensive experiments, the inventors have found out that various combinations of preservative type, concentration and other parameters were effective when used with decapsulated *Artemia* cysts and optionally carrier material, with respect to the type of predatory arthropod. For example, a range of up to 0.25%, e.g., 0.1%-0.25% methylparaben was found to enhance the effective feeding duration of the decapsulated *Artemia* cysts without damaging the fecundity of *A. swirskii*, while a concentration of 0.5% methylparaben reduced the fecundity of *A. swirskii*, while potassium sorbate had a broader range of concentrations that did not reduce the fecundity of *A. swirskii*—illustrating the detailed experimentation required to reach the disclosed effective treatment platform 100 and/or feeding elements 120 with preservatives.

Figure 11A:
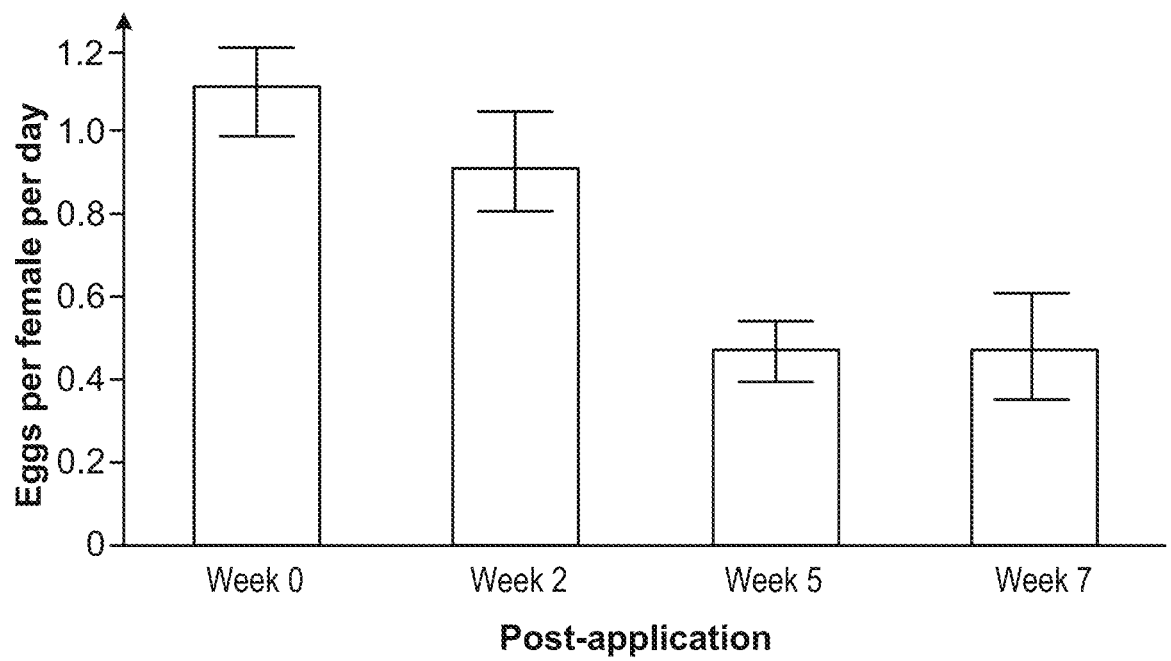
FIGS. 11A and 11B present experimental results concerning the post-application durability of the decapsulated *Artemia* cysts, according to some embodiments of the invention.
Figure 11B:
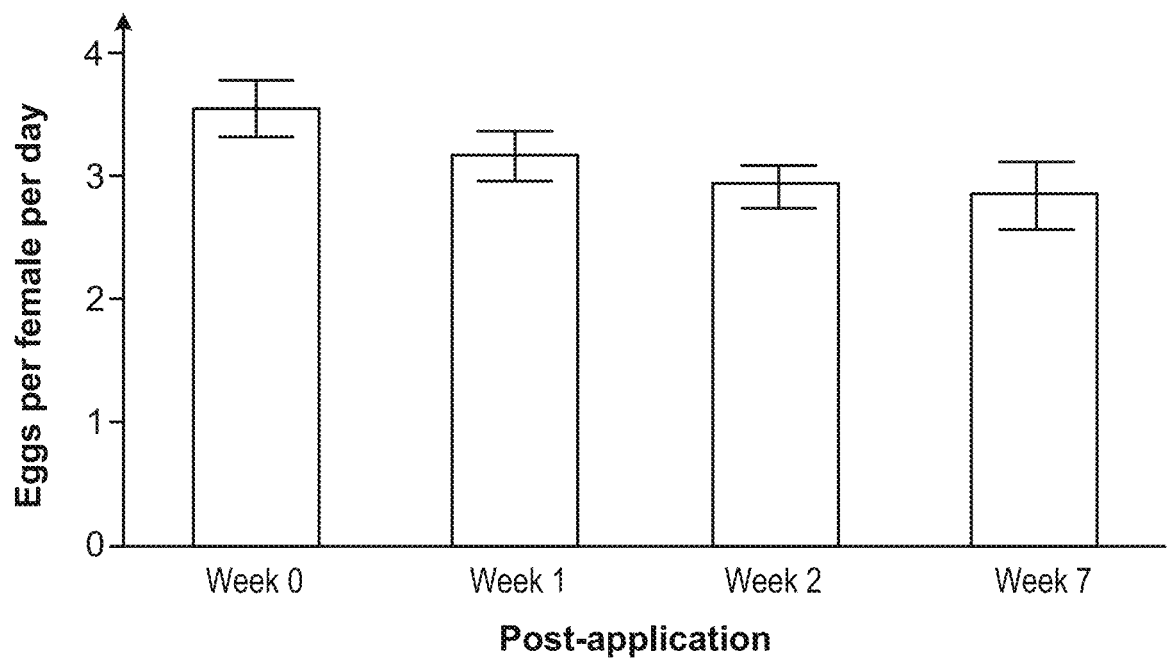

FIGS. 11A and 11B present experimental results concerning the post-application durability of the decapsulated *Artemia* cysts, according to some embodiments of the invention. FIG. 11A presents the post application durability in terms of the fecundity of *A. swirskii* feeding on disclosed decapsulated *Artemia* cysts (made of *Artemia* cysts having 80% H %) that were applied on platforms 100 and incubated in the greenhouse for different periods, under conditions of 70% average relative humidity and average temperature 21° C. FIG. 11B presents the post application durability in terms of the fecundity of *O. laevigatus* feeding on disclosed decapsulated *Artemia* cysts (made of *Artemia* cysts having 80% H %) that were applied on platforms 100 and incubated in the greenhouse for different periods, under conditions of 70% average relative humidity and average temperature 21° C.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A platform for maintaining a population of natural enemies on plants, prior and/or parallel to an occurrence of respective prey pests, the platform comprising:
    at least one mechanical support with attached feeding elements for the natural enemies, wherein the feeding elements comprise dried decapsulated *Artemia* cysts that are dried to maintain a hatching percentage (H %) larger than 30% for feeding the natural enemies,
    visual indicators and/or olfactory cues associated with the feeding elements—to attract the natural enemies thereto, and
    filamentous protrusions, artificial domatia, internal cavities, fibers and/or egg laying substrates for the natural enemies.

2. The platform of claim 1, wherein the at least one mechanical support comprises at least one of: at least one strap, at least one card, at least one sachet and a plurality of distributable elements.

3. The platform of claim 1, wherein the feeding elements are attached to the mechanical support at an adhesive region of the mechanical support.

4. The platform of claim 1, wherein the natural enemies comprise at least one of: phytoseiid predatory mites, mirid predatory bugs, anthocorid minute pirate bugs, lacewings and/or syrphid flies.

5. The platform of claim 1, wherein the at least one mechanical support further comprises attachment elements configured to attach the mechanical support to the plants.

6. The platform of claim 1, further comprising eggs of the natural enemies attached to the at least one mechanical support.

7. The platform of claim 1, wherein the dried decapsulated *Artemia* cysts having a hatching percentage (H %) larger than 80% and are effective as feed for at least two weeks post application under average relative humidity which is up to 80%.

8. The platform of claim 1, wherein the feeding elements further comprise at least one of: live or inactivated eggs of prey insects or mites, live prey mites or insects and/or their respective diets, alternative prey species, pollen, decapsulated shrimp cysts, carbohydrate nutrients and artificially composed diets designed to feed natural enemies, and wherein the at least one mechanical support comprises at least one elongated strap having a length to width ratio of at least 10:1 and configured to span a plurality of crop plants and having adhesive parts therealong, to which the feeding elements are attached.

9. The platform of claim 8, wherein the natural enemies comprise at least one of: phytoseiid predatory mites, mirid predatory bugs, anthocorid minute pirate bugs, lacewings and/or syrphid flies.

10. The platform of claim 8, wherein the platform further comprises visual indicators and/or olfactory cues associated with the feeding elements—to attract the natural enemies thereto.

11. The platform of claim 8, wherein the at least one mechanical support further comprises attachment elements configured to attach the mechanical support to the plants.

12. The platform of claim 8, wherein the at least one mechanical support further comprises filamentous protrusions, artificial domatia, internal cavities, fibers and/or egg laying substrates for the natural enemies—to attract the natural enemies thereto.

13. The platform of claim 8, wherein the at least one mechanical support further comprises multiple small mechanical supports which are smaller than 10 cm, have the attached feeding elements, configured to be blown onto the plants and have form(s) configured to be easily attachable to the plants.

* * * * *